(12) United States Patent
Arkinstall et al.

(10) Patent No.: US 7,541,375 B2
(45) Date of Patent: Jun. 2, 2009

(54) AZOLE DERIVATIVES AND PHARMACEUTICAL COMPOSITIONS CONTAINING THEM

(75) Inventors: Stephen J. Arkinstall, Belmont, MA (US); Antonio Arulanandam, Winchester, MA (US); Xuliang Jiang, Braintree, MA (US); Sharad Magar, Canton, MA (US); Roustem Nabioullin, South Burlington, VT (US); John Yingsheng Zhang, Foxboro, MA (US); Peter Blume-Jensen, Newton, MA (US)

(73) Assignee: Laboratoires Serono SA, Coinsins (CH)

( * ) Notice: Subject to any disclaimer, the term of this patent is extended or adjusted under 35 U.S.C. 154(b) by 0 days.

(21) Appl. No.: 11/782,251

(22) Filed: Jul. 24, 2007

(65) Prior Publication Data

US 2007/0293555 A1   Dec. 20, 2007

Related U.S. Application Data

(62) Division of application No. 10/491,902, filed as application No. PCT/US02/33963 on Oct. 23, 2002, now Pat. No. 7,253,199.

(60) Provisional application No. 60/336,040, filed on Oct. 23, 2001.

(51) Int. Cl.
  *A61K 31/415* (2006.01)
  *C07D 233/00* (2006.01)
(52) U.S. Cl. .................. 514/385; 548/300.1; 548/311.1
(58) Field of Classification Search ................ 514/385; 548/300.1, 311.1
  See application file for complete search history.

(56) References Cited

U.S. PATENT DOCUMENTS

| 6,579,872 B1 | 6/2003 | Brown et al. |
| 6,599,910 B1 | 7/2003 | Adams et al. |
| 7,253,199 B2 * | 8/2007 | Arkinstall et al. ........... 514/385 |

FOREIGN PATENT DOCUMENTS

| WO | 99/59959 | 11/1999 |
| WO | 00/10563 | 3/2000 |

OTHER PUBLICATIONS

Julie A. Spicer, Expert Opin. Drug Discov., vol. 3(7), 2008, 801-817, especially p. 812.*
K. Murali Krishna Rao, et al., Journal of Toxicology and Environmental Health, Part A, vol. 65, pp. 757-768, 2002.
Carl Johanson, et al., ACTA Endocrinologica, vol. 117, pp. 497-506, 1988.
Johannes L. Bos, Cancer Research, vol. 49, pp. 4682-4689, Sep. 2, 1989.
Vimala S. Sivaraman, et al., J. Clin. Invest. vol. 99, No. 7, pp. 1478-1483, 1997.
Georg Schett, et al., Arthritis & Rheumatism, vol. 43, No. 11, pp. 2501-2512, 2000.
Shella M. Thomas, et al., Cell, vol. 68, pp. 1031-1040, Mar. 20, 1992.
Kenneth W. Wood, et al., Cell, vol. 68, pp. 1041-1050, Mar. 20, 1992.
Elisabeth Genot, et al., Current Opinion in Immunology, vol. 12, pp. 289-294, 2000.
Sam J. Mansour, et al., Science, vol. 265, pp. 966-970, Aug. 12, 1994.
C. Dominique Toran-Allerand, et al., Frontiers in Neuroendocrinology, vol. 20, pp. 97-121, 1999.
Sally Cowley, et al., Cell, vol. 77, pp. 841-852, Jun. 17, 1994.
Mariano Barbacid, Ann. Rev. Biochem. vol. 56, pp. 779-827, 1987.
Korotkikh, M. Synthesis of 2- and 5-unsubstituted imidazole salts, Ukrainskii Khimicheskii Zhurnal, 2001, vol. 67, Issues 11-12, pp. 97-103. See STN Notes.
Sommerdijk, J.A.J.M. Aziridines as Precursors for Chiral Amide-Containing Surfactants, J. Org. Chem., 1997, vol. 62, pp. 4955-4960, expecially p. 4958.

* cited by examiner

*Primary Examiner*—Golam M. M. Shameem
*Assistant Examiner*—Susannah Chung
(74) *Attorney, Agent, or Firm*—Oblon, Spivak, McClelland, Maier & Neustadt, P.C.

(57) ABSTRACT

The invention provides substituted pyrazolidinone compounds, and methods of treatment and pharmaceutical compositions that utilize or comprise one or more such compounds. Compounds of the invention are useful for a variety of therapies, including treating or preventing various cancers, inflammation, septic shock, preterm labor, infertility, pain, and ischemia, and other diseases and disorders associated with MEK-1 and/or ERK-2 activation.

26 Claims, 1 Drawing Sheet

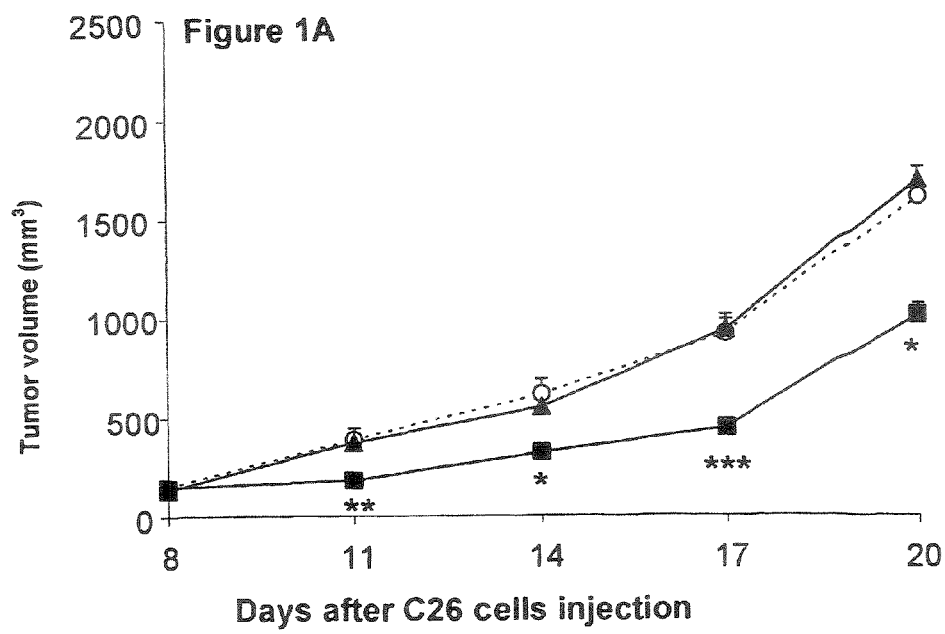
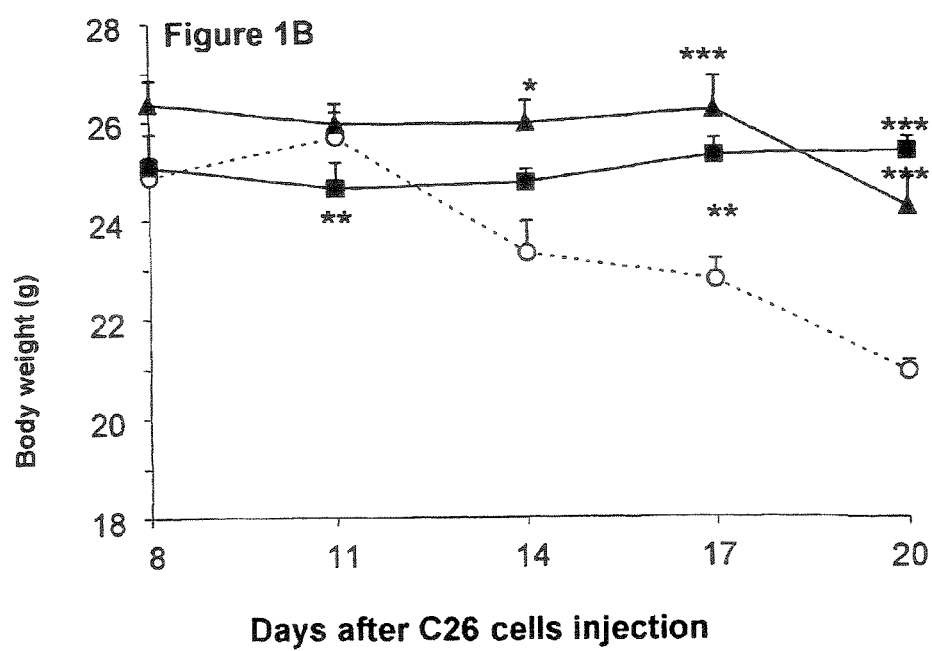

AZOLE DERIVATIVES AND PHARMACEUTICAL COMPOSITIONS CONTAINING THEM

CROSS-REFERENCE TO RELATED APPLICATIONS

This application is a divisional of U.S. application Ser. No. 10/491,902, filed on Apr. 16, 2004, which is a National Stage (371) of PCT/US02/33963, filed on Oct. 23, 2002, which claims priority to U.S. Provisional Application Ser. No. 60/336,040, filed on Oct. 23, 2001.

BACKGROUND OF THE INVENTION

1. Field of the Invention

The present invention relates to N-substituted pyrroles, pyrazoles, imidazoles, triazoles and tetrazoles, and methods of treatment and pharmaceutical compositions that utilize or comprise one or more such compounds. Compounds of the invention are useful for a variety of therapies, including treating and preventing cancer, inflammation, autoimmune diseases, pulmonary disease, septic shock, pain, preterm labor, weight loss disorders and infertility, and other diseases and disorders associated with MEK-1 and/or ERK-2.

2. Background

Chronic activation of the small C-protein Ras following growth factor signaling or activating mutations of H-, K- or N-Ras can lead to oncogenic transformations of several distinct cell types. M. Barbacid, *Ann Rev. Biochem.*, 56:779 (1987) and J. L. Bos, *Cancer Res.*, 49:4682 (1989). Overexpression and/or activation of the MAP kinase ERK-2 is associated with several disease states that include cancer and a variety of immune disorders. V. S. Sivaram et al., *J. Clin. Invest.*, 99:1478 (1997); G. Schett et al., *Arthritis Rheum.*, 43:2501 (2000); E. Genot. Et al., *Curr. Opin. Immunol.*, 12:289 (2000); S. Cowley et al., *Cell*, 77:841 (1994); and S. J. Mansour et al., *Science*, 265:966 (1994).

ERK-2 activation in such diseases is mediated by upstream activators MEK-1 (MAP kinase kinase), RAF-1 (MAP kinase kinase kinase) and Ras. See S. M. Thomas et al., *Cell*, 68:1031 (1992); and K. M. Wood et al., *Cell*, 68: 1041 (1992).

It would be desirable to have compositions that can modulate MEK-1 and/or ERK-2 activity.

SUMMARY OF THE INVENTION

We have now found N-substituted N-substituted pyrrole, pyrazole, imidazole, triazole and tetrazole compounds that are useful for a variety of therapies, including alleviating or preventing diseases and disorders mediated or otherwise associated with ERK-2 or MEK-1.

Compounds of the invention have at least one nuclear nitrogen ring substituent that is branched (particularly at least one tertiary or quaternary carbon) and have one or more hetero atoms (N, O or S, preferably O or N) and one or more aromatic groups, preferably an optionally substituted carbocyclic group such as an optionally substituted phenyl moiety or an optionally substituted heteroaromatic group.

Generally preferred for use in the therapeutic methods of the invention are substituted N-substituted pyrrole, pyrazole, imidazole, triazole and tetrazole compounds of the following Formula I:

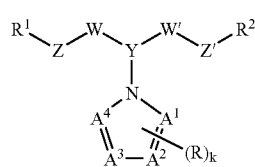

wherein each of $A^1$, $A^2$, $A^3$ and $A^4$ is carbon or nitrogen, with at least one of $A^1$, $A^2$, $A^3$ and $A^4$ being carbon;

each R is independently halo, nitro, optionally substituted alkyl preferably having 1 to about 20 carbons; optionally substituted alkenyl preferably having from 2 to about 20 carbons; optionally substituted alkynyl preferably having from 2 to about 20 carbons; optionally substituted heteroalkyl preferably having from 1 to about 20 carbons; optionally substituted heteroalkenyl preferably having from 2 to about 20 carbons; optionally substituted heteroalkynyl preferably having from 2 to about 20 carbons, optionally substituted alkanol; optionally substituted carbocyclic aryl; optionally substituted heteroalicyclic; optionally substituted heteroaromatic; optionally substituted aralkyl; optionally substituted heteroarylalkyl; and optionally substituted heteroalicyclicalkyl;

or two R groups on adjacent ring atoms are taken together with those ring to form a fused alicyclic, heteroalicylic, carbocyclic aryl or heteraromatic group having from 4 to about 8 ring members;

k is an integer, i.e. 0 (where available ring positions are each fully hydrogen-substituted where valences permit) to the maximum permitted by the valence of the ring members, and typically k is 0, 1 or 2;

Y is optionally substituted alkyl preferably having 1 to about 20 carbons; optionally substituted alkenyl preferably having from 2 to about 20 carbons; optionally substituted alkynyl preferably having from 2 to about 20 carbons; optionally substituted heteroalkyl preferably having from 1 to about 20 carbons; optionally substituted heteroalkenyl preferably having from 2 to about 20 carbons; or optionally substituted heteroalkynyl preferably having from 2 to about 20 carbons;

W and W' are each independently optionally substituted a hetero atom (particularly O or N), heteroalkyl preferably having from 1 to about 20 carbons; optionally substituted heteroalkenyl preferably having from 2 to about 20 carbons; and optionally substituted heteroalkynyl preferably having from 2 to about 20 carbons;

Z and Z' are each independently alkanoyl (i.e. a group containing a keto (>C=O) moiety) or chemical bond;

$R^1$ and $R^2$ are each independently optionally substituted carbocyclic aryl or optionally substituted heteroaromatic; and pharmaceutically acceptable salts thereof Generally preferred compounds of the invention have a branched carbon (tertiary or quaternary) proximate to the pyrrole, pyrazole, imidazole, triazole or tetrazole ring, e.g. where the branched carbon is within one, two or three carbons of the ring nitrogen of the pyrrole, pyrazole, imidazole, triazole and tetrazole group.

More particularly, preferred compounds include those of the following Formula II:

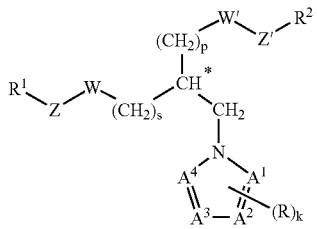

wherein $A^1$, $A^2$, $A^3$, $A^4$, each R, k, W, W', Z, Z' $R^1$ and $R^2$ are the same as defined in Formula I above; s and p are the same or different and are zero or a positive integer, and preferably s and p are zero, 1, 2 or 3; and pharmaceutically acceptable salts thereof.

Particularly preferred compounds of the invention include esters and amides of the following Formulae III and IV:

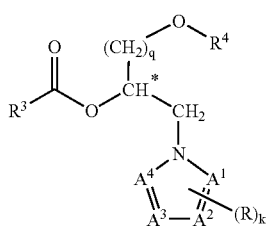

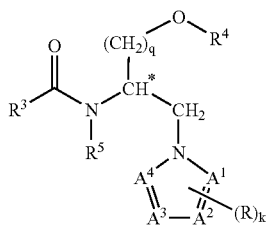

wherein in each of Formulae III and IV:

$A^1$, $A^2$, $A^3$, $A^4$, each R, and k are the same as defined in Formula I, and preferably k is zero or one;

q is a positive integer, suitably from 1 to about 12, preferably 1 to about 6, more preferably 1, 2 or 3, still more preferably q is 1;

$R^3$ and $R^4$ are each optionally substituted carbocyclic aryl or optionally substituted heteroaromatic, and preferably $R^3$ and $R^5$ each has 5 or 6 ring members such as optionally substituted phenyl;

$R^5$ is optionally substituted alkyl preferably having 1 to about 20 carbons; optionally substituted alkenyl preferably having from 2 to about 20 carbons; optionally substituted alkynyl preferably having from 2 to about 20 carbons; optionally substituted heteroalkyl preferably having from 1 to about 20 carbons; optionally substituted heteroalkenyl preferably having from 2 to about 20 carbons; or optionally substituted heteroalkynyl preferably having from 2 to about 20 carbons; optionally substituted carbocyclic aryl or optionally substituted heteroaromatic; and pharmaceutically acceptable salts thereof.

Preferred compounds of Formulae III and IV include those where q is one or two, more preferably where q is one (i.e. single methylene group).

Preferred compounds of the above include imidazole compounds, i.e. where $A^2$ is nitrogen, and $A^1$, $A^3$ and $A^4$ are each carbon.

More particularly preferred embodiment of the invention include esters and amides of the following Formulae V and VI:

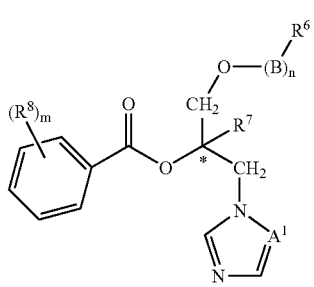

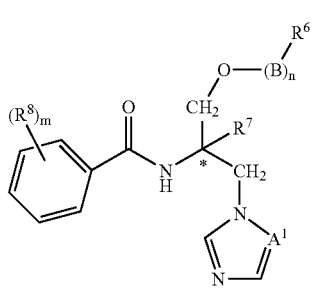

wherein $A^1$ is N or $CR^9$ and $R^9$ is H, optionally branched $C_1$-$C_6$ alkyl, optionally substituted $C_1$-$C_6$ alkyl, optionally substituted aryl or halogen;

B is —C(O)—

$R^6$ is optionally branched $C_1$-$C_6$ alkyl, optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl;

$R^7$ is H or optionally substituted $C_1$-$C_6$ alkyl;

$R^8$ is optionally substituted $C_1$-$C_6$ alkyl, optionally substituted $C_1$-$C_6$ alkoxy, optionally substituted aryl or halogen;

n is 0 or 1;

m is 1 or 2;

A particularly preferred embodiment of the invention is triazoles of formula V or VI wherein $A^1$ is N; $R^6$ is optionally branched $C_1$-$C_6$ alkyl, optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl; $R^7$ is H or optionally substituted $C_1$-$C_6$ alkyl, preferably H; $R^8$ is at least on the para position on the phenyl ring it is attached to and is optionally substituted $C_1$-$C_6$ alkyl, optionally substituted $C_1$-$C_6$ alkoxy or halogen; n is 0; m is 1 or 2.

More particularly preferred embodiment of the invention include esters and amides of the following Formulae VII and VIII:

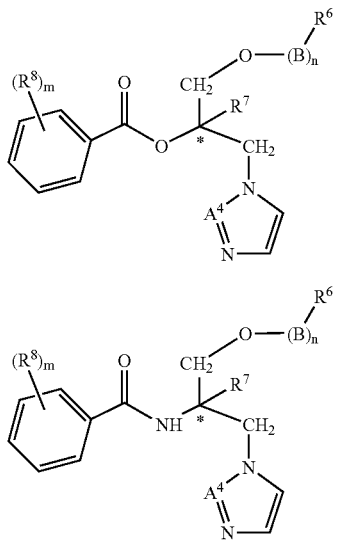

wherein $A^4$ is $CR^9$ and $R^9$ is H, optionally branched $C_1$-$C_6$ alkyl, optionally substituted $C_1$-$C_6$ alkyl, optionally substituted aryl or halogen;

B is —C(O)—

$R^6$ is optionally branched $C_1$-$C_6$ alkyl, optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl;

$R^7$ is H or optionally substituted $C_1$-$C_6$ alkyl;

$R^8$ is optionally substituted $C_1$-$C_6$ alkyl, optionally substituted $C_1$-$C_6$ alkoxy, optionally substituted aryl or halogen;

n is 0 or 1;

m is 1 or 2;

A particularly preferred embodiment of the invention is imidazoles of formula VII wherein $A^4$ is $CR^9$ and $R^9$ is H, optionally substituted $C_1$-$C_6$ alkyl, optionally substituted aryl, preferably phenyl or halogen; $R^6$ is optionally branched $C_1$-$C_6$ alkyl, optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl; $R^7$ is H or optionally substituted $C_1$-$C_6$ alkyl; $R^8$ is at least on the para position on the phenyl ring it is attached to and is optionally substituted $C_1$-$C_6$ alkyl optionally substituted $C_1$-$C_6$ alkoxy or halogen; n is 0 or 1; m is 1 or 2;

Another particularly preferred embodiment of the invention is imidazoles of formula VII wherein $A^4$ is $CR^9$ and $R^9$ is H, optionally substituted $C_1$-$C_6$ alkyl or halogen; $R^6$ is optionally substituted aryl, preferably optionally substituted phenyl or optionally substituted heteroaryl $R^7$ is H; $R^8$ is at least on the para position on the phenyl ring it is attached to and is optionally substituted $C_1$-$C_6$ alky, optionally substituted $C_1$-$C_6$ alkoxy or halogen; n is 0; m is 1 or 2;

A particularly preferred embodiment of the invention is imidazoles of formula VIII wherein $A^4$ is $CR^9$ and $R^9$ is H, optionally substituted $C_1$-$C_6$ alky, preferably methyl, optionally substituted aryl, preferably phenyl or halogen; $R^6$ is optionally branched $C_1$-$C_6$ alkyl optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl; $R^7$ is H or optionally substituted $C_1$-$C_6$ alkyl; $R^8$ is at least on the para position on the phenyl ring it is attached to and is optionally substituted $C_1$-$C_6$ alkyl, optionally substituted $C_1$-$C_6$ alkoxy or halogen; n is 0 or 1; m is 1 or 2;

Another particularly preferred embodiment of the invention is imidazoles of formula VIII wherein $A^4$ is $CR^9$ and $R^9$ is H, optionally substituted $C_1$-$C_6$ alkyl or halogen; $R^6$ is optionally substituted aryl, preferably optionally substituted phenyl or optionally substituted heteroaryl; $R^7$ is H; $R^8$ is at least on the para position on the phenyl ring it is attached to and is optionally substituted $C_1$-$C_6$ alkyl, optionally substituted $C_1$-$C_6$ alkoxy or halogen; n is 0; m is 1 or 2.

Excluded from compounds of the formulae I, II, II, IV, V, VI, VII and VI, are the following esters that are compounds from combinatorial chemistry librairies for which no use is disclosed: benzoic acid 4-methoxy-, 1-(1H-imidazol-1-ylmethyl)-2-phenoxyethyl ester (Rn=329726-55-8, INTERCHIM INTERMEDIATES); benzoic acid 4-chloro-, 1-(1H-imidazol-1-ylmethyl)-2-phenoxyethyl ester (Rn=313372-20-2, TIMTEC); 1H-imidazol-1-ethanol, .alpha.-(phenoxymethyl)-, benzoate (Rn=304869-90-7, TIMTEC).

The invention also includes compounds and use of optically active compounds of the above Formulae, particularly compounds of Formulae II, III or IV where a stereoisomer of the depicted chiral carbon (i.e. chiral carbon indicated by * in the above formulae structures) is present in an enaniomeric excess, e.g. where an stereosiomer is present in an amount of at least 70 mole percent relative to other stereosiomer(s), more preferably where one stereoisomer is present in an amount of at least about 80, 85, 90, 92, 93, 94, 95, 96, 97, 98 or 99 mole percent relative to other stereosiomer(s).

Preferred compounds of the invention exhibit good binding activity in a standard MEK-1 inhibitor assay. Such an assay is defined in Example 38, which follows.

As discussed above, N-substituted pyrrole, pyrazole, imidazole, triazole and tetrazole compounds of the invention are useful for treatment of diseases and disorders associated with MEK-1 and ERK2.

Compounds of the invention are particularly useful for treatment of a mammal suffering from or susceptible to (prophylactic therapy) cancer inclusive of solid tumors and disseminated cancers, tissue/organ transplantation, septic shock (bacteremia and cytokine induced), pain including chronic pain such as neuropathic and inflammatory pain, and preterm labor.

Compounds of the invention also are useful to treat mammalian infertility, e.g. a female suffering from or susceptible to insufficient luteinizing hormone and/or follicle-stimulating hormone levels. In addition, compounds of the invention are useful in treating erectile dysfunction in males.

Compounds of the invention also are useful for treatment of a subject suffering from or susceptible to a condition associated with ischemia, particularly cerebral ischemia. For instance, a compound of the invention may be administered to a subject suffering from or susceptible to stroke, heart attack, brain or spinal cord injury, or other ischemia-related injury or insult or condition.

Compounds of the invention are also useful to treat a subject suffering from or susceptible to an autoimmune disorder or disease (multiple sclerosis), destructive bone disorder (e.g. osteoporosis), bacterial infection, allergies, angiogenc disorders, organ hypoxia, vascular hyperplasia, cardiac hypertrophy, thrombin-induced platelet aggregation, conditions associated with prostaglandin synthase-2, pancreatitis, asthma, chronic obstructive pulmonary disease, ARDS, glomerulonephritis, rheumatoid arthritis, SLE, scleroderma, thyroiditis, Graves' disease, gastritis, diabetes, hemolytic anemia, inflammatory bowel disease, ulcerative colitis, Crohn's disease, psoriasis, graft vs host disease, osteoarthritis, Shigelloosis, edema, fever, ocular neovascularization, infantile hemangiomas and/or weight loss disorders/diseases including cachexia due to cancer or Acquired Immunodeficiency Syndrome.

Therapeutic methods of the invention in general comprise administering an effective amount of one or more substituted pyrrole, pyrazole, imidazole, triazole and tetrazole compounds as disclosed herein to a mammal in need thereof.

In a further aspect, the invention provides use of a compound of Formulae I, II, III, IV, V, VI, VII and or VIII, for the treatment or prevention (including prophylactic treatment) of a disease or condition as disclosed herein, including treatment or prevention of cancer, inflammation, autoimmune disease, bone diseases/disorders, septic shock, infertility, preterm labor, pain, or an ischemia associated condition, or other disease or disorder associated with MEK-1 or ERK-2, and other diseases and disorders disclosed herein.

In a yet further aspect, the invention provides use of a compound of Formulae I, II, III, IV, V, VI, VII and/or VIII, for the preparation of a medicament for the treatment or prevention (including prophylactic treatment) of a disease or condition as disclosed herein, including treatment or prevention of cancer, inflammation, septic shock, infertility including erectile dysfunction, preterm labor, pain, or an ischemia associated condition, or other disease or disorder associated with MEK-1 or ERK-2, and other diseases and disorders disclosed herein.

The invention also provides pharmaceutical compositions that comprise one or more N-substituted pyrrole, pyrazole, imidazole, triazole and tetrazole compounds of the invention and a suitable carrier for the compositions. Other aspects of the invention are disclosed infra.

DETAILED DESCRIPTION OF THE INVENTION

We have now discovered that N-substituted pyrrole, pyrazole, imidazole, triazole and tetrazole compounds, including compounds of the above Formulae I, II, III, IV, V, VI, VII and/or VIII are useful for treatment of a variety of disorders, particularly diseases and disorders associated with MEK-1 or ERK-2. Preferred N-substituted pyrrole, pyrazole, imidazole, triazole and tetrazole compounds are potent inhibitors of MEK-1 and/or ERK-2, as may be assessed e.g. in a standard in vitro assay.

Suitable alkyl substituent groups of compounds of the invention (which includes compounds of Formulae I, II, III, IV, V, VI, VII and/or VIII as those formulae are defined above) typically have from 1 to about 12 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2, 3, 4, 5, or 6 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1, 2, 3, 4, 5 or 6 carbon atoms. Preferred alkylthio groups of compounds of the invention include those groups having one or more thioether linkages and from 1 to about 12 carbon atoms, more preferably from 1 to about 8 carbon atoms, and still more preferably 1, 2, 3, 4, 5, or 6 carbon atoms. Preferred alkylsulfinyl groups of compounds of the invention include those groups having one or more sulfoxide (SO) groups and from 1 to about 12 carbon atoms, more preferably from 1 to about 8 carbon atoms, and still more preferably 1, 2, 3, 4, 5, or 6 carbon atoms. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1, 2, 3, 4, 5 or 6 carbon atoms. Preferred aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole. Suitable heteroalicyclic groups of compounds of the invention contain one or more N, O or S atoms and include, e.g., tetrahydrofuranyl, thienyl, tetrahydropyranyl, piperidinyl, morpholino and pyrrolidinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, and 2,4-substituted phenyl; and substituted naphthyl, including naphthyl substituted at the 5, 6 and/or 7 positions.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaromatic groups, where such groups are substituted onto an alkyl linkage. More preferably, a heteroaralkyl group contains a heteroaromatic group that has 1 to 3 rings, 3 to 8 ring members in each ring and from 1 to 3 hetero (N, O or S) atoms, substituted onto an alkyl linkage. Suitable heteroaromatic groups substituted onto an alkyl linkage include e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable heteroalicyclicalkyl groups of compounds of the invention include single and multiple ring compounds, where such groups are substituted onto an alkyl linkage. More preferably, a heteroalicyclicalkyl group contains at least one ring that has 3 to 8 ring members from 1 to 3 hetero (N, O or S) atoms, substituted onto an alkyl linkage. Suitable heteroalicyclic groups substituted onto an alkyl linkage include e.g. tetrahydrofuranyl, thienyl, tetrahydropyranyl, piperidinyl, morpholino and pyrrolidinyl groups.

The term "heteroalkyl" as used herein is inclusive of alkoxy, alkylthio, alkylamino, alkylsulfinyl and alkylsulfonyl. The term "heteroalkenyl" as used herein is inclusive of such alkoxy, alkylthio, alkylamino, alkylsulfinyl and alkylsulfonyl groups that further include one or more carbon-carbon double bonds, typically one or two carbon-carbon double bonds, The term "heteroalkynyl" as used herein is inclusive of such alkoxy, alkylthio, alkylamino, alkylsulfinyl and alkylsulfonyl groups that further include one or more carbon-carbon triple bonds, typically one or two carbon-carbon triple bonds.

As discussed above, R, $R^1$, $R^2$, W, W', Z, Z'; $R^3$, $R^4$ and $R^5$ groups are optionally substituted. A "substituted" R, $R^1$, $R^2$, W, W', Z, Z'; $R^3$, $R^4$ and $R^5$ group or other substituent may be substituted by other than hydrogen at one or more available positions, typically 1 to 3 or 4 positions, by one or more suitable groups such as those disclosed herein. Suitable groups that may be present on a "substituted" R, $R^1$, $R^2$, W, W', Z, Z'; $R^3$, $R^4$ and $R^5$ group or other substituent include e.g. halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons; aralkyl having 1 to 3 separate or fused rings and from 6 to about 18 carbon ring atoms, with benzyl being a preferred group; aralkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

Preferred ring substituents of carbocyclic or heteroaromatic groups of compounds of the invention include hydroxy; halogen (F, Cl, Br and I); azido; nitro; optionally substituted alkyl having 1 to about 12 carbons such as methyl, ethyl, propyl and butyl and branched groups such as isopropyl, sec-butyl and tert-butyl, and including halogenated alkyl, particularly fluoro-alkyl having 1 to about 6 carbon atoms; optionally substituted alkoxy having 1 to about 12 carbons such as methoxy, ethoxy, propoxy and butoxy, and including halogenated alkoxy; optionally substituted alkylthio having 1 to about 6 carbons such as methylthio and ethylthio; optionally substituted alkylsulfinyl having 1 to about 6 carbons such as methylsulfinyl (—S(O)$CH_3$) and ethylsulfinyl (—S(O)$CH_2CH_3$); optionally substituted alkylsulfonyl having 1 to about 6 carbons such as methylsulfonyl (—S(O)$_2CH_3$) and ethylsulfonyl (—S(O)$_2CH_2CH_3$); carboxy (—COOH) and alkanoyl such as alkanoyl having one or more keto groups and 1 to about 12 carbons such as formyl (—C(=O)H), acetyl, and the like.

More particularly preferred embodiment of the invention includes esters and amides of the following Formulae V and VI:

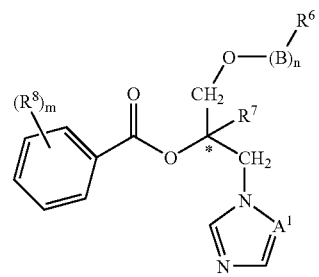

V

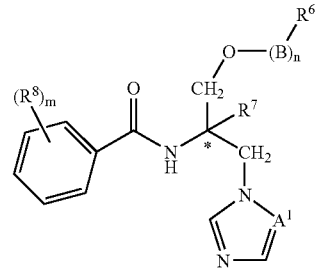

VI wherein $A^1$ is N or $CR^9$ and $R^9$ is H, optionally substituted $C_1$-$C_6$ alkyl, optionally substituted aryl or halogen;

B is —C(O)—

$R^6$ is optionally branched $C_1$-$C_6$ alkyl, preferably methyl, optionally substituted $C_3$-$C_6$ cycloalkyl $C_1$-$C_6$ alkyl, preferably cyclopropylmethyl, optionally substituted $C_3$-$C_6$ heterocycloalkyl, e.g. tetrahydropyranyl, optionally substituted aryl, e.g. phenyl, iodophenyl, fluorophenyl, acetylamino phenyl, nitrophenyl, t-bu phenyl, cyanophenyl or optionally substituted heteroaryl, e.g. pyridinyl, cyanopyridinyl, nitropyridinyl;

$R^7$ is H or optionally substituted $C_1$-$C_6$ alkyl, preferably H or methyl;

$R^8$ is optionally substituted $C_1$-$C_6$ alkyl, preferably, $CF_3$, optionally substituted $C_1$-$C_6$ alkoxy, e.g. methyloxy or halogen, e.g. I, Br, Cl;

n is 0 or 1;

m is 1 or 2;

A preferred embodiment of the invention is triazoles of formula V wherein $A^1$ is N; $R^6$ is optionally substituted aryl, preferably optionally substituted phenyl or optionally substituted heteroaryl; $R^7$ is H or optionally substituted $C_1$-$C_6$ alkyl, preferably H; $R^8$ is at least on the para position on the phenyl ring it is attached to and is optionally substituted $C_1$-$C_6$ alkyl, optionally substituted $C_1$-$C_6$ alkoxy or halogen; n is 0; m is 1 or 2.

More particularly preferred embodiment of the invention include esters and amides of the following Formulae VII and VIII:

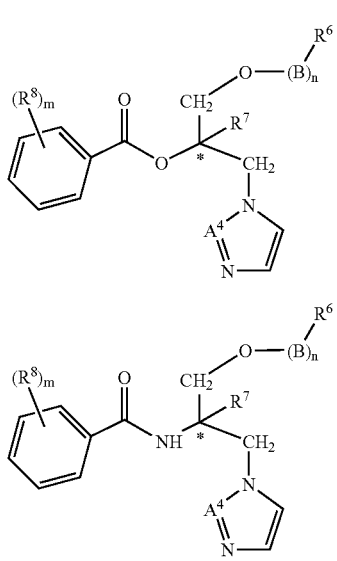

VII

VIII wherein $A^4$ is $CR^9$ and $R^9$ is H, optionally branched $C_1$-$C_6$ alkyl, optionally substituted $C_1$-$C_6$ alkyl, optionally substituted aryl or halogen;

B is —C(O)—

$R^6$ is optionally branched $C_1$-$C_6$ alkyl, optionally substituted $C_3$-$C_6$ cycloalkyl $C_1$-$C_6$ alkyl, optionally substituted $C_3$-$C_6$ heterocycloalkyl optionally substituted aryl or optionally substituted heteroaryl;

$R^7$ is H or optionally substituted $C_1$-$C_6$ alkyl;

$R^8$ is optionally substituted $C_1$-$C_6$ alkyl, optionally substituted $C_1$-$C_6$ alkoxy, optionally substituted aryl or halogen;

n is 0 or 1;

m is 1 or 2;

A more preferred embodiment of the invention includes imidazoles of formulae VII and VIII wherein $A^4$ is $CR^9$ with $R^9$ is H, optionally branched $C_1$-$C_6$ alkyl, optionally substituted aryl or halogen, B is —C(O)—; $R^6$ is optionally branched $C_1$-$C_6$ alkyl, preferably methyl, optionally substituted $C_3$-$C_6$ cycloalkyl $C_1$-$C_6$ alkyl, preferably cyclopropylmethyl, optionally substituted $C_3$-$C_6$ heterocycloalkyl, e.g. tetrahydropyranyl, optionally substituted aryl, e.g. phenyl, iodophenyl, fluorophenyl, acetylamino phenyl, nitrophenyl, t-bu phenyl, cyanophenyl or optionally substituted heteroaryl, e.g. pyridinyl, cyanopyridinyl, nitropyridinyl; $R^7$ is H or optionally substituted $C_1$-$C_6$ alkyl, preferably H or methyl; $R^8$ is optionally substituted $C_1$-$C_6$ alkyl, preferably, $CF_3$, optionally substituted $C_1$-$C_6$ alkoxy, e.g. methyloxy or halogen, e.g. I, Br, Cl; n is 0 or 1; m is 1 or 2;

A particularly preferred embodiment of the invention is imidazoles of formula VII wherein $A^4$ is $CR^9$ with $R^9$ is H, optionally substituted $C_1$-$C_6$ alkyl preferably methyl or halogen, preferably Cl, most preferably H; $R^6$ is optionally substituted aryl, preferably optionally substituted phenyl or optionally substituted heteroaryl, preferably substituted pyridinyl wherein the aryl and heteroaryl rings are preferably substituted by a group selected from H, halogen, e.g. I or F, $NO_2$, t-bu, NH—C(O)$CH_3$, cyano; $R^7$ is H; n is 0 or 1; m is 1 or 2;

A particularly preferred embodiment of the invention is imidazoles of formula VII wherein $A^4$ is $CR^9$ with $R^9$ is H, optionally substituted $C_1$-$C_6$ alkyl preferably methyl or halogen, preferably Cl, most preferably H; $R^6$ is optionally substituted aryl, preferably optionally substituted phenyl or optionally substituted heteroaryl, preferably substituted pyridinyl wherein the aryl and heteroaryl rings are preferably substituted by a group selected from H, halogen, e.g. I or F, $NO_2$, t-bu, NH—C(O)$CH_3$, cyano; $R^7$ is H; n is 0; m is 1 or 2;

Another particularly preferred embodiment of the invention is imidazoles of formula VIII wherein $A^4$ is $CR^9$ with $R^9$ is H, optionally substituted $C_1$-$C_6$ alky, preferably methyl or halogen, preferably Cl; $R^6$ is optionally substituted aryl, preferably optionally substituted phenyl or optionally substituted heteroaryl, preferably optionally substituted pyridinyl; $R^7$ is H or optionally substituted $C_1$-$C_6$ alkyl, preferably H or methyl; $R^8$ is at least on the para position on the phenyl ring it is attached to and is optionally substituted $C_1$-$C_6$ alkyl, preferably CF3, optionally substituted $C_1$-$C_6$ alkoxy, preferably methoxy or halogen, preferably Br, I, Cl, most preferably I, n is 0 or 1; m is 1 or 2;

An another particularly preferred embodiment of the invention is imidazoles of formula VIII wherein $A^4$ is $CR^9$ with $R^9$ is H, optionally substituted $C_1$-$C_6$ alkyl preferably methyl or halogen, preferably Cl, most preferably H; $R^6$ is optionally substituted aryl, preferably optionally substituted phenyl or optionally substituted heteroaryl, preferably substituted pyridinyl wherein the aryl and heteroaryl rings are preferably by a group selected among H, halogen, preferably I, F, $NO_2$, t-bu, NH—C(O)$CH_3$, cyano; $R^7$ is H; n is 0; m is 1 or 2.

It should be understood that alkoxy, alkylthio, alkylsulfinyl, alkylsulfonyl and aminoalkyl substituent groups described above include groups where a hetero atom is directly bonded to a ring system, such as a carbocyclic aryl group or heteroaromatic group or heteroalicyclic group including an N-substituted pyrrole, pyrazole, imidazole, triazole and/or tetrazole group, as well as groups where a hetero atom of the group is spaced from such ring system by an alkylene linkage, e.g. of 1 to about 4 carbon atoms.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"$C_3$-$C_6$-cycloalkyl" refers to saturated or partially unsaturated carbocyclic rings having 3 to 6 carbon atoms. Examples include cyclopropyl, cyclobutyl, cyclopentyl, cyclohexyl, cyclohexenyl and the like.

"$C_3$-$C_6$-heterocycloalkyl" refers to saturated or partially unsaturated rings having 3 to 6 atoms and containing at least one heterotom selected from N, S and O. Examples include pyrrolidinyl, piperidinyl, piperazinyl, imidazolidinyl, morpholinyl, tetrahydropyranyl and the like.

"$C_3$-$C_6$-cycloalkyl $C_1$-$C_6$-alkyl" refers to $C_1$-$C_6$-alkyl groups having an $C_3$-$C_6$-cycloalkyl substituent, such as, for example methyl-cyclopropane, ethyl-cyclohexane and the like.

"Aryl" refers to an unsaturated aromatic carbocyclic group of from 6 to 14 carbon atoms having a single ring (e.g. phenyl) or multiple condensed rings (e.g. naphthyl). Examples of aryl include phenyl, naphthyl, phenanthrenyl and the like.

"Heteroaryl" refers to a monocyclic heteromatic, or a bicyclic or a tricyclic fused-ring heteroaromatic group. Particular examples of heteroaromatic groups include optionally substituted pyridyl, pyridinyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"Enantiomeric excess" (ee) refers to the percent excess of the enantiomer over the racemate in a mixture of a pure enantiomer (R or S) and a racemate (RS) as defined below.

$$ee = 100\% \times (|R-S|)/(R+S) = |\% R - \% S|$$

where R represents the number of moles of R enantiomer in the sample and S represents the number of moles of S enantiomer in the sample, and |R−S| represents the Absolute Value of the difference of R and S. Compounds of the invention can be obtained in an "Enantiomeric excess" by a synthesis comprising an enantioselective step or can be isolated by for example, crystallization or chiral HPLC.

A particularly preferred embodiment includes compounds of the invention in an enantiomeric excess of the R enantiomer, of at least at or about 50, 70, 80 or 90%, with degree of preference increasing with the increasing ee of the R enantiomer.

In the absence of an enantiomeric synthesis, racemic products are usually obtained that do however also have the inventive set out activity as MEK-1 and or ERK-2 inhibitors.

Specifically preferred compounds of the invention include the following compounds and pharmaceutically acceptable salts of such compounds, and optically active stereoisomers (enaniomerically enriched mixtures) of such compounds. Set forth below is the compound name and, in many instances, the chemical structure of the compound is depicted directly above the compound name, with a preferred stereoisomer shown in some structures.

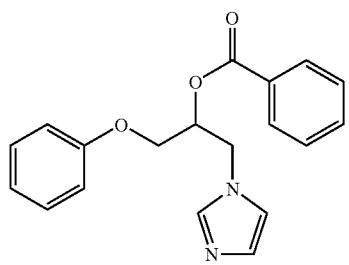

benzoic acid 1-imidazol-1-yl methyl-2-phenoxy-ethyl ester;

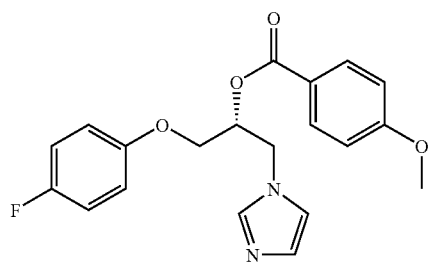

4-methoxy-benzoic acid 1-imidazol-1-yl methyl-2-(4-fluorophenoxy)-ethyl ester;

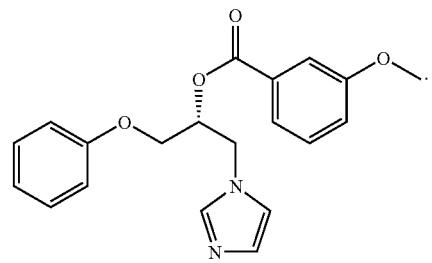

3-methoxy-benzoic acid 1-imidazol-1-yl methyl-2-phenoxy-ethyl ester;

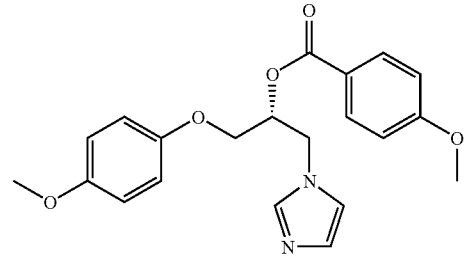

4-methoxy-benzoic acid 1-imidazol-1-yl methyl-2-(4-methoxy phenoxy)-ethyl ester;

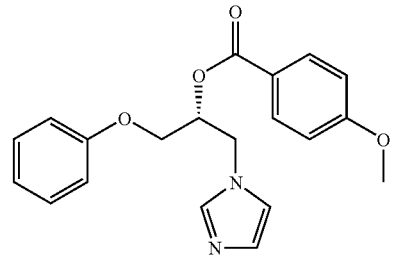

(R) 4-methoxy-benzoic acid 1-imidazol-1-yl methyl-2-phenoxy-ethyl ester;

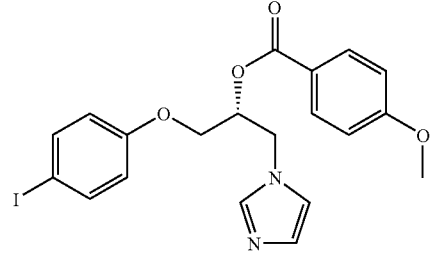

4-methoxy-benzoic acid 1-imidazol-1-yl methyl-2-(4-iodophenoxy)-ethyl ester;

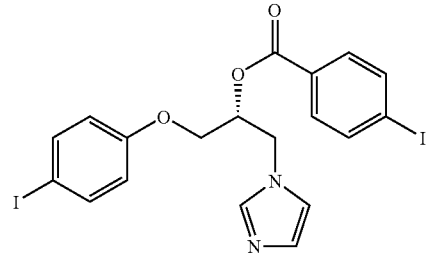

4-iodo-benzoic acid 1-imidazol-1-yl methyl-2-(4-iodo phenoxy)-ethyl ester;

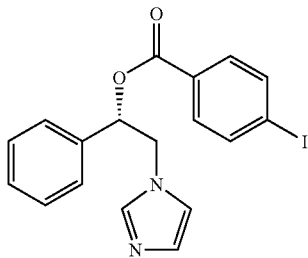

4-iodo-benzoic acid 2-imidazol-1-yl-1-phenyl-ethylester

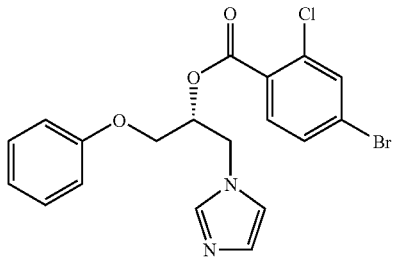

4-bromo-2-chloro-benzoic acid 1-imidazol-1-yl methyl-2-phenoxy-ethyl ester;

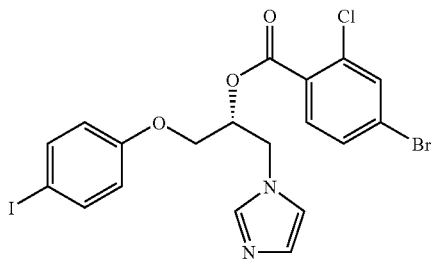

4-bromo-2-chloro-benzoic acid 1-imidazol-1-yl methyl-2-(4-iodophenoxy)-ethylester;

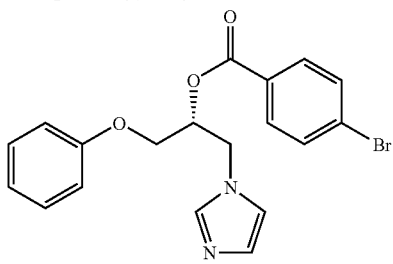

4-bromo-benzoic acid 1-imidazol-1-yl methyl-2-phenoxy-ethyl ester;

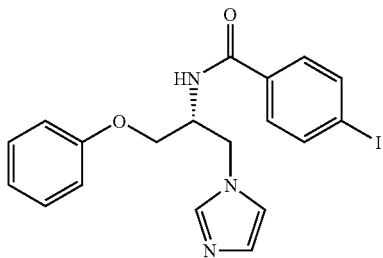

N-(1-imidazol-1-yl methyl-2-phenoxy-ethyl)-4-iodo-benzamide;
4-trifluoromethyl-benzoic acid 1-imidazol-1-yl methyl-2-phenoxy-ethyl ester;
4-chloro-benzoic acid 1-imidazol-1-yl methyl-2-phenoxy-ethyl ester;
N-(1-imidazol-1-yl methyl-2-phenoxy-ethyl)-4-methoxy-benzamide;
4-iodo-benzoic acid 1-imidazol-1-yl methyl-2-phenoxy-ethyl ester;
4-iodo-benzoic acid 1-imidazol-1-yl methyl-2-(4-fluorophenoxy)-ethyl ester;
4-fluoro-benzoic acid 1-imidazol-1-yl methyl-2-phenoxy-ethyl ester;
N-[(1-imidazol-1-yl methyl)-2-phenoxy-ethyl)]-N-methyl-4-iodo-benzamide;
N-[(1-imidazol-1-yl methyl)-2-(4-fluorophenoxy-ethyl)]-N-methyl-4-iodo-benzamide;
4-Iodo-benzoic acid 2-(4-fluoro-phenoxy)-1-[1,2,4]triazol-1-ylmethyl-ethyl ester (R-isomer);
4-Iodo-benzoic acid 2-(4-acetylamino-phenoxy)-1-imidazol-1-ylmethyl-ethyl ester (R-isomer);
N-[2-(4-Fluoro-phenoxy)-1-imidazol-1-ylmethyl-ethyl]-4-iodo-benzamide (R-isomer);
N-[2-(4-tert-Butyl-phenoxy)-1-imidazol-1-ylmethyl-ethyl]-4-iodo-benzamide;
4-Iodo-benzoic acid 2-imidazol-1-yl-1-(3-nitro-phenoxymethyl)-ethyl ester (R-isomer);
4-Iodo-benzoic acid 2-imidazol-1-yl-1-(2-nitro-phenoxymethyl)-ethyl ester (R-isomer);
4-Iodo-benzoic acid 1-(4-nitrobenzoyloxymethyl)-2-imidazol-1-yl-1-methyl-ethyl ester (R-isomer);
4-Iodo-benzoic acid 2-imidazol-1-yl-1-(4-nitro-phenoxymethyl)-ethyl ester (R-isomer);
4-Iodo-benzoic acid 1-imidazol-1-ylmethyl-2-methoxy-ethyl ester (R-isomer);
4-Iodo-benzoic acid 1-(2-methyl-imidazol-1-ylmethyl)-2-(tetrahydro-pyran-2-yloxy)-ethyl ester;
N-[2-(4-Fluoro-phenoxy)-1-[1,2,4]triazol-1-ylmethyl-ethyl]-4-iodo-benzamide;
4-Iodo-benzoic acid 1-imidazol-1-yl methyl-2-(pyridin-3-yloxy)-ethyl ester (R-isomer);
2,4-Dichloro-benzoic acid 2-(4-fluoro-phenoxy)-1-imidazol-1-ylmethyl-ethyl ester (R-isomer);
4-Iodo-benzoic acid 1-(4-cyano-phenoxymethyl)-2-imidazol-1-yl-ethyl ester;
4-Iodo-benzoic acid 1-(4-cyano-phenoxymethyl)-2-(2-methyl-imidazol-1-yl)-ethyl ester (R-isomer);
2-Chloro-N-[2-(4-fluoro-phenoxy)-1-imidazol-1-ylmethyl-ethyl]-4-iodo-benzamide (R-isomer);
N-[2-(4-Fluoro-phenoxy)-1-(2-methyl-imidazol-1-ylmethyl)-ethyl]-4-iodo-benzamide (R-isomer);
2-Chloro-4-iodo-benzoic acid 1-cyclopropylmethoxymethyl-2-(2-methyl-imidazol-1-yl)-ethyl ester (R-isomer);
N-[1-(2-Chloro-imidazol-1-ylmethyl)-2-(4-fluoro-phenoxy)-ethyl]-4-iodo-benzamide (R-isomer);
N-[2-(4-Fluoro-phenoxy)-1-imidazol-1-ylmethyl-ethyl]-3-iodo-benzamide;
N-[2-(4-Fluoro-phenoxy-1-tetrazol-1-ylmethyl-ethyl]-4-iodo-benzamide;
2-Chloro-N-[2-imidazol-1-yl-1-(pyridin-3-yloxymethyl)-ethyl]-4-iodo-benzamide;
N-[2-Imidazol-1-yl-1-(pyridin-3-yloxymethyl)-ethyl]-4-iodo-benzamide;
N-[2-(4-Fluoro-phenoxy)-1-(2-phenyl-imidazol-1-ylmethyl)-ethyl]-4-iodo-benzamide;
N-[1-(2-Chloro-imidazol-1-ylmethyl)-2-(4-cyano-phenoxy)-ethyl]-4-iodo-benzamide;
N-[2-Imidazol-1-yl-1-(3-nitro-pyridin-2-yloxymethyl)-ethyl]-4-iodo-benzamide;
N-[2-Imidazol-1-yl-1-(4-nitro-phenoxymethyl)-ethyl]-4-iodo-benzamide;
N-[1-(3-Cyano-pyridin-2-yloxymethyl)-2-imidazol-1-yl-ethyl]-4-iodo-benzamide;

N-[1-(5-Cyano-pyridin-2-yloxymethyl)-2-imidazol-1-yl-ethyl]-4-iodo-benzamide;
N-[1-(4-Cyano-phenoxymethyl)-2-imidazol-1-yl-ethyl]-4-iodo-benzamide;
N-[-(4-Cyano-phenoxymethyl)-2-(2-methyl-imidazol-1-yl)-ethyl]-4-iodo-benzamide; and N-[1-(2-Difluoromethyl-imidazol-1-ylmethyl)-2-(4-fluoro-phenoxy)-ethyl]-4-iodo-benzamide.

Compounds of the invention can be readily prepared. For instance, the base nitrogen heterocycle, i.e. optionally substituted pyrrole, pyrazole, imidazole or triazole, can be reacted with an electrophilic reagent, such as a substituted oxirane. The resulting reaction product, e.g. an alcohol-substituted imidazole, can be further functionalized as desired. For instance, the hydroxy of the alcohol-substituted nitrogen heterocycle can be further reacted, e.g. reacted with an optionally substituted benzoic acid to provide a carbocyclic aryl ester. Alternatively, the hydroxy can undergo a substitution reaction, e.g. by reaction with an azide (such as through a mesylate, tosylate, etc.), which then can be reduced to an amine and reacted with an optionally substituted carbocyclic aryl acid such as optionally substituted benzoic acid to provide an amide.

Substitution to the oxirane reagent can provide substituents $R^1$, W and $R^3$ groups as those groups are defined in the above formula. Functionalization of the hydroxy group provided upon oxirane ring-opening can provide groups $R^2$, W', Z, X and $R^4$ as those groups are defined in the formula above.

A preferred synthetic sequence is shown in Scheme I below, where formation of the carbocyclic aryl or heteroaryl glycidyl ether I.4 is suitably carried out by Mitsunobu reaction of the appropriately substituted phenol with glycidol I.3, which is then treated with imidazole or desired nucleophilic nitrogen heterocycle (pyrazole, imidazole, triazole or a tetrazole) to obtain a secondary alcohol (R)-I.5 followed by esterification with aryl carboxylic acid. This last esterification step can be carried out in the presence of 1,3-dicyclohexylhexyl carbodiimide (DCC) or other similar coupling agents.

Scheme I

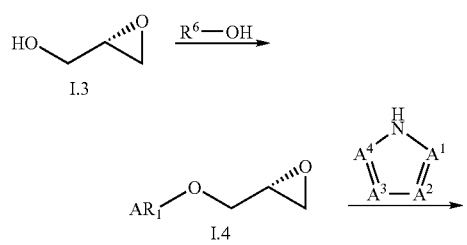

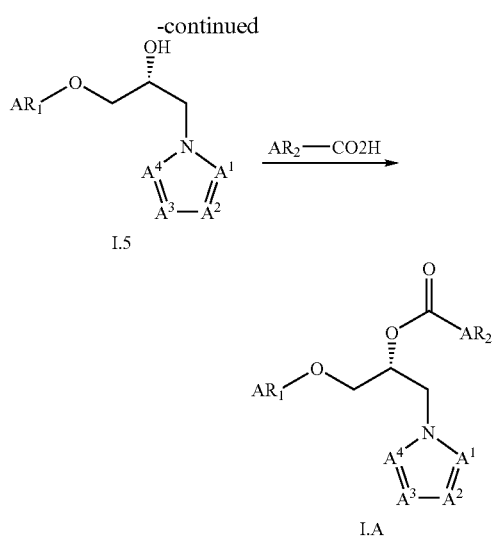

Aryloxy ethyl benzamides of compounds of the invention of formula I.A. i.e of formula III wherein $AR_1$ is $R^4$, $AR_2$ is $R^3$, q is 1 and k is 0 or of formula V wherein $AR_1$ is $R^6$, $AR_2$ is .Phe$(R^8)_m$, $R^7$ is H and n is 0 can be suitably prepared via several different routes from the intermediate secondary alcohol I.5.

As generally depicted in Scheme II below, one method involves converting the alcohol (S)-I.5 to azide II.7 by nucleophilic substitution reaction of diphenylphosphoryl azide with alcohol in the presence of triphenylphosphine (PPh$_3$) and diethylazodicarboxylate (DEAD). The same azide can also be obtained in two steps by first converting the alcohol to a suitable leaving group such as mesylate, tosylate or halide followed by nucleophilic substitution with sodium azide in an aprotic polar solvent. Reduction of the azide to amine II.8 is accomplished by a hydride reagent or triphenylphosphine, which is followed by coupling with a carboxylic acid to afford the final amide product.

Additionally, compound II.6 with activated carbon (e.g. sulfonyl ester as shown) can be converted to an amine II.8.

The amine II.8 can be further functionalized as desired, e.g. reacted with an acid to provide the corresponding amide of formula II.A, i.e. of formula IV wherein $AR_1$ is $R^4$, $AR_2$ is $R^3$, $R^5$ is R, q is 1 and k is 0 or of formula VI wherein $AR_1$ is $R^6$, $AR_2$ is .Phe$(R^8)_m$, $R^7$ is H and n is 0 as generally depicted in the following Scheme II.

Scheme II

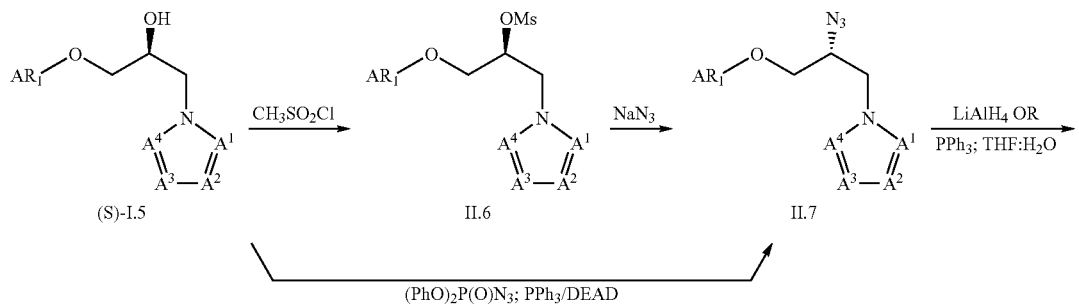

-continued

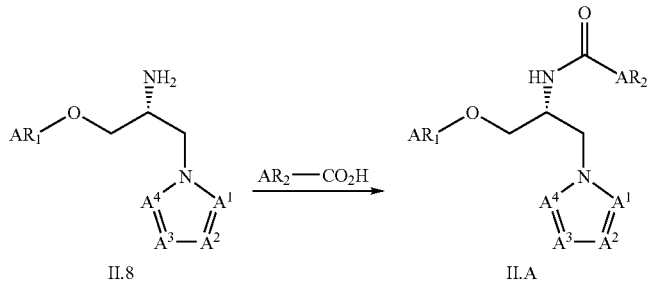

As shown in Scheme III below, the amine intermediate II.8 can also be obtained from (S)-I. 5 by treatment of the alcohol with equimolar amounts of phthalimide, Ph₃P and diethyl azodicarboxylate at room temperature followed by hydrolysis of the phthalimide by heating with hydrazine in an exchange reaction.

Scheme III

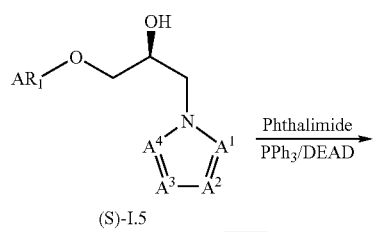

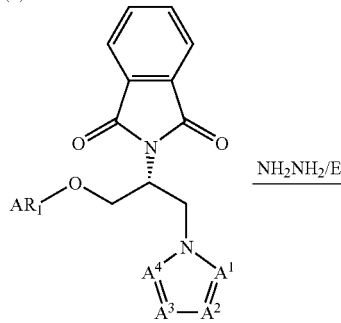

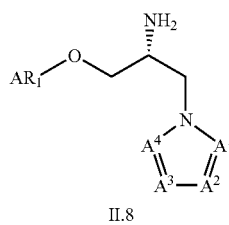

In the reactions of the above Schemes, the product can be suitably isolated by removing the solvent by evaporation under reduced pressure, and further purified, if needed, by standard methods such as chromatography, crystallization or distillation.

Bi-ester derivatives of compounds of the invention of formula IV.A. i.e of formula V wherein $AR_1$ is $.Phe(R^8)_m$, $AR_2$ is $R^6$, $R^7$ is H or alkyl and n is 1 can be suitably prepared from the intermediate secondary alcohol IV.2, which in turn can be obtained by imidazole-mediated epoxide opening of commercially available aryl esters IV.1 such as benzoate, 4-nitro benzoate, 4-t-butyl benzoate, etc.

Scheme IV

The various substituent groups shown in the above Schemes I through IV have the same meaning as corresponding groups specified in the above formulae.

Specifically preferred syntheses of compounds of the invention are detailed in the examples which follow.

As discussed above, preferred compounds of the invention exhibit good activity in a standard in vitro MEK-1 inhibition assay. References herein to "standard MEK-1 inhibition assay" are intended to refer to the protocol as defined in Example 38, which follows. Generally preferred compounds of the invention exhibit single dose inhibition of MEK-1 in that assay of less than about 5,000 (nM) more preferably less than about 2,000 (nM), still more preferably less than about 1000 or 500 (nM), even more preferably less than about 100 (nM), yet more preferably less than about 50, 20 or 10 (nM), in such a defined standard MEK-1 inhibition assay as exemplified by Example 38 which follows.

As indicated above, the present invention includes methods for treating or preventing MEK-1 and/or ERK-2 mediated or associated diseases or disorders.

The compounds of the invention will be useful in a variety of cancers. Specifically, cancers caused by molecular changes that ultimately result in deregulated MEK-ERK signaling will be inhibited by described compounds. Hence, cancers caused by activating mutations of Raf (examples include, but are not limited to, NSCL cancer, pancreatic cancer, ovarian cancer, and malignant melanoma), of Ras (examples include, but are not limited to, NSCL cancer, pancreatic cancer, colon cancer, mammary carcinoma, ovarian cancer, endometrial, bladder cancer, malignant melanoma, seminomas, and thyroid cancers) are inhibited by our compounds. An additional important group of diverse cancers that are responsive and inhibited by our compounds are all the cancers caused by activating mutations in receptor and non-receptor protein tyrosine kinases, that signal through the MEK-ERK signaling pathway. Examples include, but are not limited to, NSCL cancer, breast cancer, glioblastoma multiforme, ovarian cancer, endometrial cancer, myeloid and lymphocytic leukemias, gastric cancers, and lymphomas.

Preferred therapeutic methods of the invention include treating malignancies, including solid tumors and disseminated cancers. Exemplar tumors that may be treated in accordance with the invention include e.g. cancers of the lung, prostate, breast, liver, colon, breast, kidney, pancreas, brain, skin including malignant melanoma, testes or ovaries, or leukemias, and including in particular multiple myeloma-related bone disorder, mestatic melanoma and malignant melanoma, and Kaposi's sarcoma, as well as the cell types and classes set forth in the examples which follow. Indeed, compounds of the invention are effective anti-proliferation against a wide range of tumor cells, as shown by the results set forth in Examples 40 through 42, which follow.

Therapeutic methods of the invention also include treating inflammation and septic shock. The invention also includes treatment of pain, including neuropathic pain and chronic inflammatory pain, Subjects (female) suffering from or susceptible to preterm labor also may be treated by administration of one or more compounds of the invention. The invention also includes treatment of mammalian infertility, including erectile dysfunction in males.

As disclosed above, compounds of the invention are also useful to treat autoimmune diseases and disorders (multiple sclerosis), destructive bone disorders (e.g. osteoporosis), bacterial infections, allergies, angiogenic disorders, organ hypoxia, vascular hyperplasia, cardiac hypertrophy, thrombin-induced platelet aggregation, conditions associated with prostaglandin synthase-2, pancreatitis, asthma, ARDS, glomerulonephritis, rheumatoid arthritis, SLE, scleroderma, thyroiditis, Graves' disease, gastritis, diabetes, hemolytic anemia, inflammatory bowel disease, ulcerative colitis, Crohn's disease, psoriasis, graft vs host disease, osteoarthritis, Shigelloosis, edema, fever, ocular neovascularization infantile hemangiomas, chronic obstructive pulmonary disease and/or weight loss diseases/disorders including cachexia due to cancer or Acquired Immunodeficiency Syndrome.

The therapeutic methods of the invention generally comprise administration of an effective amount of one or more compounds of the invention to a subject including a mammal, such as a primate, especially a human, in need of such treatment.

The compounds of the invention will be useful in a variety of inflammatory disorders. It has been established in recent reports (Yiao, Yi Qun, et al, Journal of Biological Chemistry, Vol 277 No. 17, pp 14884-14893, 2002 and Rutault, K., et al, Journal of Biological Chemistry Vol 276 No 9, pp 6666-6674, 2001) that release of pro-inflammatory cytokines, PGE2, COX2 and other molecules in response to stimuli including, but not limited to, LPS, collagen trauma, neuropeptides, vasoactive peptides etc., is MEK-ERK-dependent. Accordingly, both acute and chronic inflammatory disorders will be susceptible to treatment with the compounds of the invention. These include, but are not limited to, reumatoid arthritis, topical exzemas and topical/local inflammatory disorders, inflammatory bowel diseases, antigen/irritant-induced eosinophilia, septic shock, chronic glomerulonephritis, astma, graft-vs-host disease and transplantation rejection.

Typical candidates for treatment in accordance with the methods of the invention persons suffering from or suspected of suffering from any of the above disorders or diseases, such as a female susceptible or suffering from preterm labor, or a subject suffering from or susceptible to an inflammatory disorder, or undergoing a transplantation procedure such as a skin graft or an organ transplant e.g. lung, heart, kidney and the like.

Compounds of the invention also will be useful to treat mammals suffering from or suspected of suffering from infertility. See the *Merck Manual*, vol. 2, pages 12-17 ($16^{th}$ ed.) for identification of patients suffering from or suspected of suffering from infertility, which in the case of humans, can include failure to conceive within one year of unprotected intercourse.

Such treatment methods of the invention may be particularly beneficial for female mammals suffering from an ovulatory disorder. Additionally, compounds of the invention can be administered to females undergoing assisted reproductive treatments such as in-vitro fertilization, e.g. to stimulate follicular development and maturation. See, for instance, the results of Example 43 which follows, where follicle-stimulating hormone production is enhanced by administration of a compound of the invention.

For such treatment of infertility and related disorders, it may be preferred to administer a compound of the invention in combination with follicle-stimulating hormone (FSH) or luteinizing hormone (LH) for simultaneous, sequential or separate use.

As discussed above, the invention also includes therapeutic methods for treatment of an ischemia related condition, such as associated with stroke, heart attack, brain or spinal cord trauma or other head or spine injury, hypoxia, hypoglycemia. Therapies of the invention are particularly useful for treatment of cerebral ischemia.

Typical subjects for treatment by such methods include e.g. subjects susceptible to or suffering from or having suffered from heart attack or stroke, neurological deficits associated with cardiac arrest or other occurrence, and patients undergoing significant surgery where brain ischemia is a potential complication. For instance, one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of one or more compounds of the present invention could be administered pre-operatively or peri-operatively to reduce such risks associated with carotid endarterectomy, or other post-surgical neuorological deficits. Methods of the invention also can be employed for treatment and/or prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of one or more compounds of the invention, typically either pre-operatively or peri-operatively.

The treatment methods of the invention also will be useful for treatment of mammals other than humans, including for veterinary applications such as to treat horses and livestock e.g. cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum cellular interstitial fluid, saliva, feces and urine) and cell and tissue samples of the above subjects will be suitable for use.

Compounds of the invention may be administered singularly (i.e. sole therapeutic agent of a regime) to treat or prevent discuses and conditions as disclosed herein.

Compounds of the invention also may be administered as a "cocktail" formulation, i.e. coordinated administration of one or more compounds of the invention together with one or more other active therapeutics. For instance, one or more compounds of the invention may be administered in coordination with a regime of a pain relief agent or an anti-inflammatory agent, or a known fertility agent such as FSH and/or LH as discussed above.

In certain preferred aspects of the invention, particularly compositional aspects of the invention, less preferred and hence excluded from such preferred aspects, particularly compositional aspects, are certain ester-based compounds having imidazole and/or phenoxy substitution, particularly the following three compounds present in racemic mixtures: 4-methoxy-benzoic acid 1-imidazol-1-yl methyl-2-phenoxy-ethyl ester, 4-chloro-benzoic acid 1-imidazol-1-yl methyl-2-phenoxy-ethyl ester, and benzoic acid 1-imidazol-1-yl methyl-2-phenoxy-ethyl ester. Hence, such less preferred compounds, particularly present in racemic mixtures, are excluded from certain preferred aspects of the invention, particularly certain preferred compositional aspects of the invention. Enantiomerically enriched mixtures of 4-methoxy-benzoic acid 1-imidazol-1-yl methyl-2-phenoxy-ethyl ester, 4-chloro-benzoic acid 1-imidazol-1-yl methyl-2-phenoxy-ethyl ester, and benzoic acid 1-imidazol-1-yl methyl-2-phenoxy-ethyl ester may be more preferred.

All compounds of Formula I are believed to be novel, with the exception of racemates of 4-methoxy-benzoic acid 1-imidazol-1-yl methyl-2-phenoxy-ethyl ester, 4-chloro-benzoic acid 1-imidazol-1-yl methyl-2-phenoxy-ethyl ester, and benzoic acid 1-imidazol-1-yl methyl-2-phenoxy-ethyl ester, which have not been suggested for pharmaceutical or therapeutic uses.

Compounds of the invention can be administered by a variety of routes, such as orally or by injection, e.g., intramuscular, intraperitoneal, subcutaneous or intravenous injection, or topically such as transdermally, vaginally and the like. Compounds of the invention may be suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc. If the compound has an acidic group, e.g. a carboxy group, base additional salts may be prepared. Lists of additional suitable salts may be found in Part 5 of *Remington's Pharmaceutical Sciences*, 20$^{th}$ Edition, 2000, Marck Publishing Company, Easton, Pa.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for oral, parenteral, enteral or topical application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

Pharmaceutical compositions of the invention include a compound of the invention packaged together with instructions (written) for therapeutic use of the compound to treat e.g. cancer, inflammation, chronic pain, infertility, preterm labor, or other disease or disorder associated with or mediated by MEK-1 and/or ERK-2.

For oral administration, pharmaceutical compositions containing one or more compounds of the invention may be formulated as e.g. tablets, troches, lozenges, aqueous or oily suspensions, dispersible powders or granules, emulsions, hard or soft capsules, syrups, elixers and the like. Typically suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For parenteral application, e.g., sub-cutaneous, intraperitoneal or intramuscular, particularly suitable are solutions, preferably oily or aqueous solutions as well as suspensions, emulsions, or implants, including suppositories. Ampoules are convenient unit dosages.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. See also *Remington's Pharmaceutical Sciences*, supra. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage.

The entire text of all documents cited herein are incorporated by reference herein. The following non-limiting examples are illustrative of the invention.

The compounds of the invention may be prepared as racemates. The racemates themselves are useful in the treatment and prevention of diseases and conditions. Compounds of the invention also may be prepared as enantiomerically enriched mixtures by chiral synthetic approaches, as are known and disclosed in e.g. March, *Advanced Organic Chemistry*, (4$^{th}$ ed. John Wiley) and J. Seyden-Penne, *Chiral Auxiliaries and Ligands in Asymmetric Synthesis* (1995 Wiley-Interscience). Alternatively, pure enantiomers, or enantiomerically enriched mixtures may be isolated by subjecting racemates or mixtures to chiral separation techniques, such as crystallization with an enantiomeric counter-ion, or chiral chromatography, or other approached as disclosed e.g. in March, *Advanced Organic Chemistry*.

DESCRIPTION OF THE FIGURE

FIG. 1: it reports the effect of Example 30 on both the growth (FIG. 1A) of tumors induced in CDF1 mice with murine colon carcinoma C26 cells and on the tumor-induced body weight loss (FIG. 1.B). Day 8 corresponds to the date of injection of the compound of the invention, i.e. 8 days after the injection of C26 cells (Protocol in Example 45).

Triangles: Group treated with Example 30 at 50 mg/kg p.o. bid.

Squares: Group treated with Example 30 at 1000 mg/kg p.o. bid.

Empty Circles: Control group treated with NP3S (5% N-methylpyrrolidone/30% PEG400/25% PEG200/120% Propylene Glycol in Saline) per os bid.

Statistical significance represented as (*) $p<0.05$; () $p<0.01$; and (*) $p<0.001$.

EXAMPLES 1-37

Syntheses of Compounds of the Invention

Syntheses of compounds of the invention having an ester substituent.

Example 1

4-Iodo-benzoic acid 1-imidazol-1-yl methyl-2-phenoxy-ethyl ester

Ester-substituted compound 1 (Example 1) was synthesized as outlined in the following Scheme.

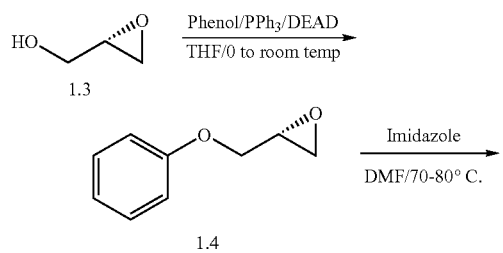

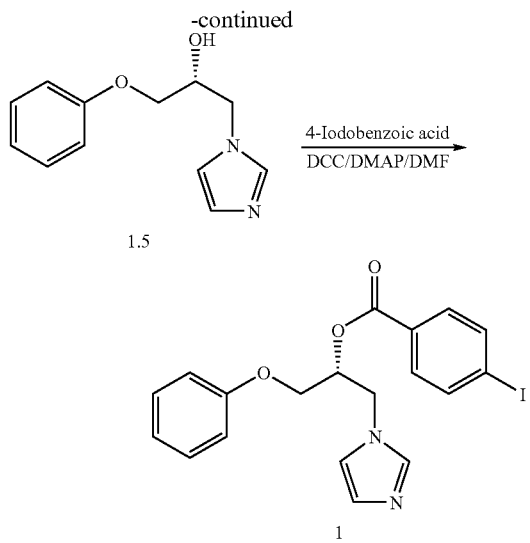

Part 1. Synthesis of Epoxide Intermediate 1.4:

Triphenylphosphine (17.7 g, 67.49 mmol) was weighed in an oven dried 500 mL round flask and 200 mL anhydrous THF was syringed in under argon. The resulting solution was stirred in an ice-water bath until all the solid was dissolved. S-(−)-Glycidol 1.3 (5 g, 67.49 mmol) in 30 mL cold THF was added into the flask and then DEAD (10.63 mL, 67.49 mmol) was added slowly under argon into the vigorously stirred reaction mixture. The color of reaction solution changed from colorless to light brown during the addition. After 10 minutes, phenol (5.77 g, 61.36 mmol) in 20 mL THF was added in. The resulting solution was stirred in the ice-water bath over-night. The completion of reaction was monitored by the disappearance of glycidol. Evaporation of THF afforded a light yellow solid, which was directly transferred onto a silica-gel column. The desired product 1.4 (light yellow oil, 9.0 g, 60.03 mmol, 97.8%) was eluted from column via hexane/EtOAc gradient (100% to 50% hexane and 0.2% TEA)

Part 2: Synthesis of Hydroxide Intermediate 1.5:

The epoxide 1.4 (9.0 g, 60.03 mol) obtained in the previous step was weighed in a 500 mL round flask and dissolved in 200 mL anhydrous DMF at room temperature. Imidazole (8.4 g, 122.72 mmol) was added to the flask and the resulting solution was vigorously stirred until all the solid was dissolved. Then the flask was placed in a 70° C. oil-bath and the reaction was run for two days under argon. After completion of reaction, DMF was evaporated and the remaining crude material was purified via column chromatography to afford 1.5 as a white solid (12 g, 55.07 mmol, 91.7%). MS (ESI-MS) M+1=219.

Part 3: Synthesis of Compound 1 (4-Iodo-benzoic acid 1-imidazol-1-yl methyl-2-phenoxy-ethyl ester):

The hydroxide 1.5 (1 g, 4.59 mmol) from previous step (Part 2) was weighed in an oven-dried 100 mL round flask. Then 4-iodobenzoic acid (1.14 g, 4.59 mmol) and 30 mL anhydrous DMF was added sequentially in the flask under argon. The resulting solution was stirred in ice-water bath till all solid dissolved. DCC (1M solution in THF, 4.59 mmol, 4.59 mL) was added in the well cooled clear solution and after 10 minutes DMAP (112 mg, 0.92 mol) was added in. The resulting solution was stirred in the ice-water bath over night. DMF was evaporated and the resulting yellow solid was purified using column chromatography (hexane/EtOAc gradient 3:1 to 1:9) to afford the desired final product 1 (Example 1), (R) 4-iodo-benzoic acid 1-imidazol-1-yl methyl-2-phenoxy-ethyl ester, as a light yellowish solid (1.6 g, 3.57 mmol, 76%).

MS (ESI-MS) M=1=449.1. $^1$H NMR (400 MHz, CDCl$_3$): δ 7.79 (d, 2H, J=8.4 Hz), 7.67 (d, 2H, J=8.4 Hz), 7.52, (s, 1H), 7.28 (t, 2H, J=7.7 Hz), 7.03-6.89 (m, 5H), 5.56 (tt, 1H, J=4.76, 4.76 Hz), 4.46 (dd, 2H, J=11.75, 4.76 Hz), 4.09 (dd, 1H, J=10.24, 4.76 Hz), 3.98 (dd, 1H, J=10.24, 4.76 Hz).

Examples 2-21

By following the general procedure for Example 1, the following esters of the invention were prepared.

| Example No. | Compound | Mass m/e |
|---|---|---|
| 2 | Benzoic acid 1-imidazol-1-yl methyl-2-phenoxy-ethyl ester (racemic) | 323.3 |
| 3 | 4-Methoxy-benzoic acid 1-imidazol-1-yl methyl-2-(4-fluorophenoxy)-ethyl ester (racemic) | 371.3 |
| 4 | 3-Methoxy-benzoic acid 1-imidazol-1-yl methyl-2-phenoxy-ethyl ester (racemic) | 353.3 |
| 5 | 4-Methoxy-benzoic acid 1-imidazol-1-yl methyl-2-(4-methoxy phenoxy)-ethyl ester | 383.3 |
| 6 | (R)-4-Methoxy-benzoic acid 1-imidazol-1-yl methyl-2-phenoxy-ethyl ester | 353.1 |
| 7 | (S)-4-Methoxy-benzoic acid 1-imidazol-1-yl methyl-2-benzyloxy-ethyl ester | 367.1 |
| 8 | (R)-4-Methoxy-benzoic acid 1-imidazol-1-yl methyl-2-(4-iodophenoxy)-ethyl ester | 479.0 |
| 9 | (R)-4-Iodo-benzoic acid 1-imidazol-1-yl methyl-2-(4-iodo phenoxy)-ethyl ester | 574.9 |
| 10 | (R)-4-Bromo-2-chloro-benzoic acid 1-imidazol-1-yl methyl-2-phenoxy)-ethyl ester | 435.1; 437.0 |
| 11 | (R)-4-Bromo-2-chloro-benzoic acid 1-imidazol-1-yl methyl-2-(4-iodo phenoxy)-ethyl ester | 561.0; 562.9 |
| 12 | (R)-4-Bromo-benzoic acid 1-imidazol-1-yl methyl-2-phenoxy-ethyl ester | 401.1; 403.1 |
| 13 | (R)-4-Trifluoromethyl-benzoic acid 1-imidazol-1-yl methyl-2-phenoxy-ethyl ester | 391.2 |
| 14 | (R)-4-Chloro-benzoic acid 1-imidazol-1-yl methyl-2-phenoxy-ethyl ester | 357.2 |
| 15 | 4-Iodo-benzoic acid 2-(4-acetylamino-phenoxy)-1-imidazol-1-ylmethyl-ethyl ester (R-isomer) | 506.2 |
| 16 | 4-Iodo-benzoic acid 2-imidazol-1-yl-1-(3-nitro-phenoxymethyl)-ethyl ester (R-isomer) | 494.0 |
| 17 | 4-Iodo-benzoic acid 2-imidazol-1-yl-1-(2-nitro-phenoxymethyl)-ethyl ester (R-isomer) | 494.0 |
| 18 | 4-Iodo-benzoic acid 2-imidazol-1-yl-1-(4-nitro-phenoxymethyl)-ethyl ester (R-isomer) | 494.0 |
| 19 | 2,4-Dichloro-benzoic acid 2-(4-fluoro-phenoxy)-1-imidazol-1-ylmethyl-ethyl ester (R-isomer) | 409.2 411.2 |
| 20 | 4-Iodo-benzoic acid 1-(4-cyano-phenoxymethyl)-2-imidazol-1-yl-ethyl ester | 474.0 |
| 21 | 4-Iodo-benzoic acid 1-(4-cyano-phenoxymethyl)-2-(2-methyl-imidazol-1-yl)-ethyl ester (R-isomer) | 488.1 |

Examples 22-26

By following the general procedure for scheme I, the following esters of the invention were prepared, starting respectively with the following materials:

Example 22

4-Iodo-benzoic acid 1-imidazol-3-yl methyl-2-(pyridin-3-yloxy)-ethyl ester

Commercially available (R)-(−)-glycidyl-3-nosylate was heated with imidazole in a microwave to afford the secondary alcohol. The nosyl group is then readily displaced by anionic 3-hydroxy pyridine to afford the pyridyl ether. The aliphatic secondary alcohol is then converted to ester of Example 22 using standard methodology Mass (ESI-MS) M+1=450.0

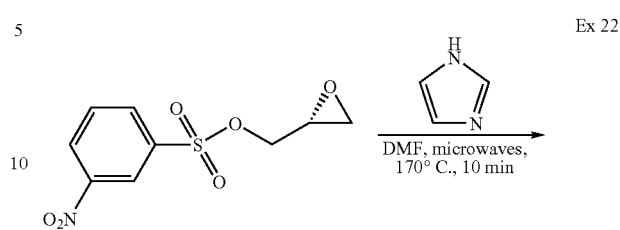

Ex 22

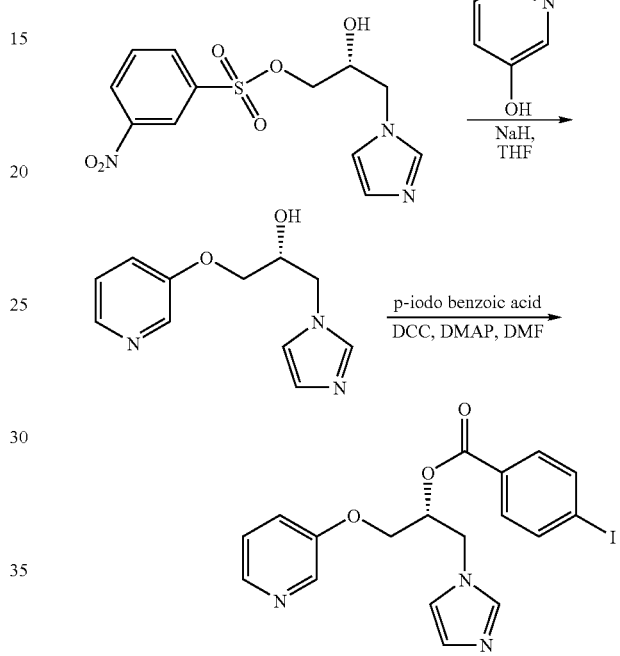

Example 23

2-Chloro-4-iodo-benzoic acid 1-cyclopropyl-methoxymethyl-2-(2-methyl-imidazol-1-yl)-ethyl ester Commercially available (R)-(−)-glycidyl tosylate was treated with hydroxymethyl cyclopropane in the presence of a base. The resulting intermediate epoxide was heated with 2-methyl imidazole to afford the secondary alcohol, which was then converted to the 4-iodobenzoate ester derivative of Example 23. Mass (ESI-MS) M+1=475.2

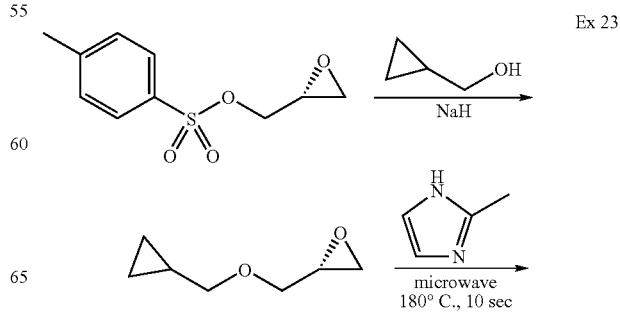

Ex 23

-continued

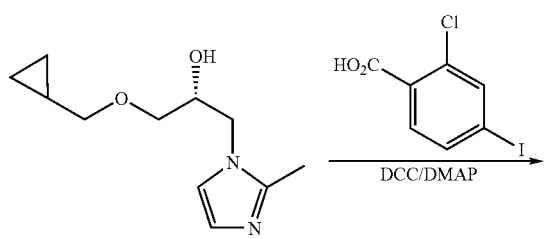

Example 24

4-Iodo-benzoic acid 1-(2-methyl-imidazol-1-yl ethyl)-2-(tetrahydro-pyran-2-yloxy)-ethyl ester Commercially available (S)-(−)-glycidol was refluxed with dihydropyran in the presence of p-toluene sulfonic acid to get the protected THP-derivative. This was heated with 2-methyl imidazole to afford the secondary alcohol, which was then converted to the 4-iodobenzoate ester derivative of Example 24. Mass (ESI-MS) M+1=471.9

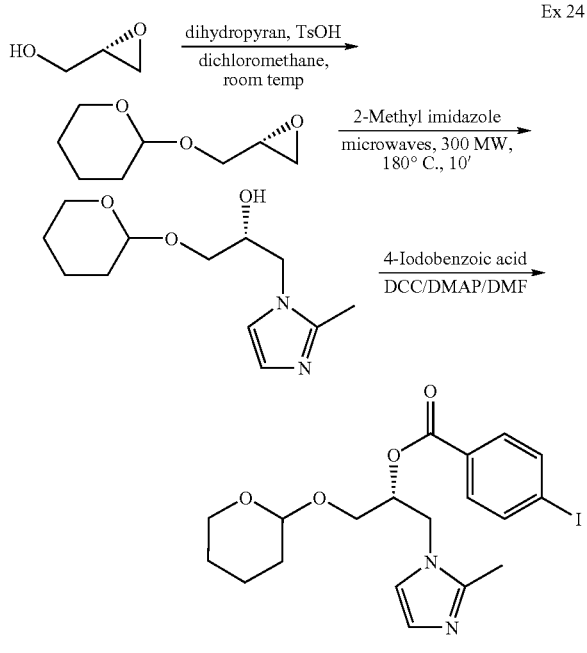

Example 25

4-Iodo-benzoic acid 1-imidazol-1-ylmethyl-2-methoxy-ethyl ester

Commercially available (R)-(−)-methyl glycidyl ether was heated with imidazole to afford the secondary alcohol, which was then reacted with 4-iodo benzoic acid in the presence of dicyclohexyl carbodiimide and 4-dimethylamino pyridine to afford 4-iodobenzoate ester derivative of Example 25. Mass (ESI-MS) M−1=384.9

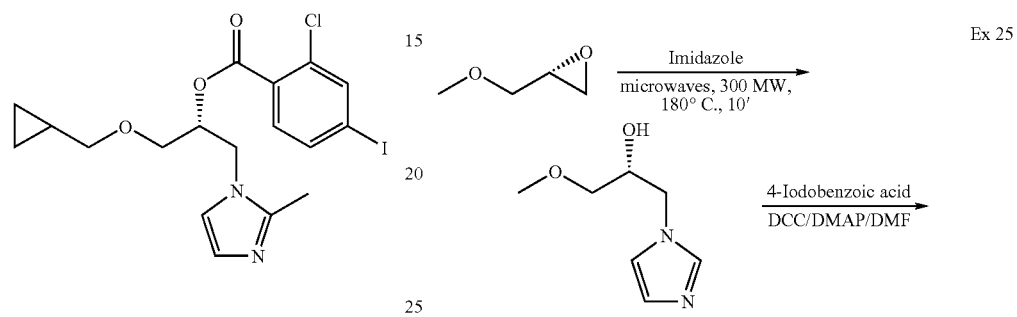

Examples 26

4-Iodo-benzoic acid 1-(4-nitrobenzoyloxymethyl)-2-imidazol-1-yl-1-methyl-ethyl ester By following the general procedure for scheme IV, the following bi-ester of the invention (Example 26) was prepared, starting with commercially available (2R)-(−)-2-methyl glycidyl 4-nitrobenzoate, which was heated with imidazole to afford the secondary alcohol followed by esterification. Mass (ESI-MS) M+1=536.0.

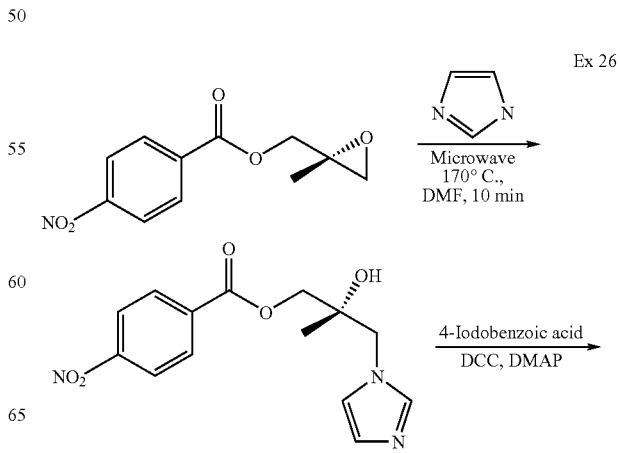

-continued

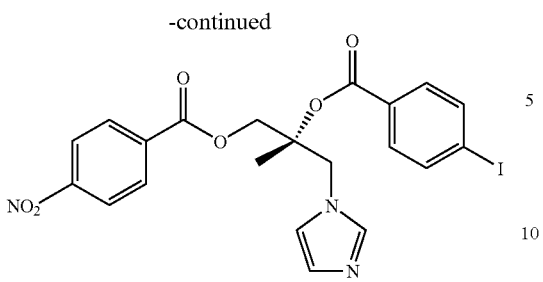

Syntheses of Compounds of the Invention Having an Amide Substituent.

Example 27

N-(1-imidazol-1-ylmethyl-2-phenoxy-ethyl)-4-iodo-benzamide

Amide-substituted compound 27 (Example 27) was synthesized as outlined in the following Scheme.

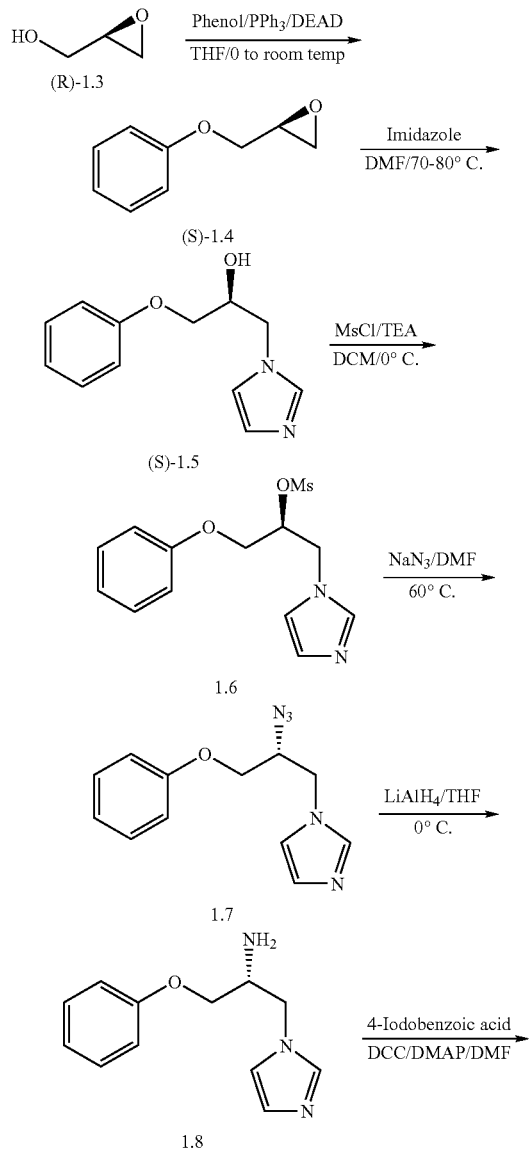

-continued

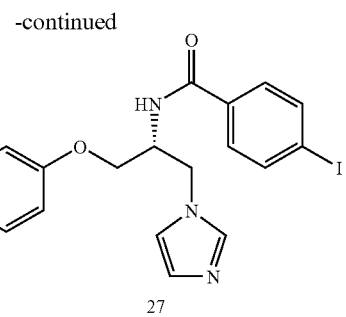

Part 1: Synthesis of Intermediates 1.4 and 1.5:

Intermediates 1.4 and 1.5 were synthesized following the procedure in Example 1 above.

Part 2: Synthesis of the Mesylate 1.6:

The hydroxyl intermediate 1.5 (3.34 g. 15.33 mmol) was weighed in a 250 mL round flask and dissolved in 120 mL anhydrous DCM in an ice-water bath. Triethylamine (2.35 mL, 16.86 mmol) and methyl sulfonyl chloride (1.31 mL, 16.86 mmol) was added sequentially to the flask. The resulting solution was vigorously stirred for 4 hours in ice-water bath. The reaction was quenched using water and extracted with DCM (3×100 mL). The combined organic phase was dried over $MgSO_4$ and evaporated to give an yellow oil, which was purified using column chromatography to give 1.6 as a light yellow oil (4.38 g, 14.82 mmol, 96.7%).

MS (ESI-MS) M+1=297.2.

Part 3: Synthesis of Azide Intermediate 1.7:

The mesylate 1.6 (4.38 g, 14.82 mmol) was weighed in a 250 mL round flask and dissolved in 120 mL anhydrous DMF at room temperature. Sodium azide (1.2 g, 18.4 mmol) was added in the flask and the resulting solution was vigorously stirred in a 60° C. oil-bath over night. After completion of reaction, DMF was evaporated and the remaining was dissolved in EtOAc and washed with water. The organic phase was dried over $MgSO_4$ and evaporated to give an yellowish solid, which was purified via column chromatography to afford azide intermediate 1.7 as a light yellow solid (3.3 g, 13.63 mmol, 92%). MS (ESI-MS) M+1=244.1.

Part 4: Synthesis of Amine Intermediate 1.8:

Azide 1.7 (1.53 g, 6.3 mmol) was weighed in a 100 mL round flask and dissolved in 40 mL anhydrous THF at room temperature under argon. The resulting solution was placed in an ice-water bath and $LiAlH_4$ (1M solution in THF, 12.6 mL, 12.6 mmol) was added slowly to the vigorously stirred solution. After 4 hours, saturated $NH_4Cl$ solution was added to quench the reaction. The resulting suspension was extracted by EtOAc (3×150 mL). The organic phases were combined, dried over $MgSO_4$ and evaporated to give a yellowish solid, which was purified via column chromatography EtOAc/Hexane 1:1, 9:1, then DCM/MeOH 4:1) to afford 18 as a light yellowish oil (1.02 g, 4.7 mmol, 74.5%). MS (ESI-MS) M+1=218.2.

Part 5: Synthesis of Compound 27 (N-(-1-imidazol-1-yl-methyl-2-phenoxy-ethyl)-4-iodo-benzamide)

Amine 1.8 (469 mg, 2.16 mmol) was weighed in an oven-dried 50 mL round flask. Then 4-iodobenzoic acid (643.2 mg, 2.59 mmol) and 20 mL anhydrous DMF was added sequentially in the flask under argon. The resulting solution was stirred in ice-water bath until all the solid was dissolved. DCC (1M solution in THF, 2.59 mmol, 2.59 mL) was added in the well-cooled clear solution and after 10 minutes DMAP (132 mg, 1.08 mmol) was added in. The resulting solution was stirred in the ice-water bath over night. DMF was evaporated and the resulting yellow solid was purified using column chromatography (hexane/EtOAc gradient 3:1 to 1:9, then DCM/MeOH 4:1) to afford 27 (Example 27) as a light yellowish solid (821 mg, 1.84 mmol, 85%). MS (ESI-MS) M+1=448.1 $^1$H NMR (400 MHz, CDCl$_3$): δ 7.73 (d, 2H, J=8.06 Hz), 7.54 (d, 2H, J=8.06 Hz), 7.31 (t, 2H, J=8.04 Hz), 7.25, (s, 1H), 7.07-7.00 (m, 3H), 6.93 (d, 2H, J=8.4 Hz), 4.82-4.78 (m, 1H), 4.59 (dd, 1H, J=13.91, 6.59 Hz), 4.40 (dd, 1H, J=13.91, 6.59 Hz), 4.11-4.04 (m, 2H).

Examples 28-36

By following the general procedure for Example 27, the following amides of the invention was prepared.

| Example No. | Compound | Mass (M + 1) |
|---|---|---|
| 28 | N-(1-Imidazol-1-yl methyl-2-phenoxy-ethyl)-4-methoxy-benzamide (racemic) | 352.1 |
| 29 | (R)-N-(1-Imidazol-1-yl methyl-2-phenoxy-ethyl)-4-methoxy-benzamide | 352.1 |
| 30 | N-[2-(4-Fluoro-phenoxy)-1-imidazol-1-ylmethyl-ethyl]-4-iodo-benzamide (R-isomer) | 466.0 |
| 31 | N-[2-(4-tert-Butyl-phenoxy)-1-imidazol-1-ylmethyl-ethyl]-4-iodo-benzamide | 504.0 |
| 32 | 2-Chloro-N-[2-(4-fluoro-phenoxy)-1-imidazol-1-ylmethyl-ethyl]-4-iodo-benzamide (R-isomer) | 500.0 |
| 33 | N-[2-(4-Fluoro-phenoxy)-1-(2-methyl-imidazol-1-ylmethyl)-ethyl]-4-iodo-benzamide (R-isomer) | 480.0 |
| 34 | N-[1-(2-Chloro-imidazol-1-ylmethyl)-2-(4-fluoro-phenoxy)-ethyl]-4-iodo-benzamide (R-isomer) | 500.3 |
| 35 | N-[1-(2-Chloro-imidazol-1-ylmethyl)-2-(4-cyano-phenoxy)-ethyl]-4-iodo-benzamide | 506.9 |
| 36 | N-[2-Imidazol-1-yl-1-(4-nitro-phenoxymethyl)-ethyl]-4-iodo-benzamide | 493.1 |

Based on the procedure for Example 27, the following amide of the invention was prepared:

Example 37

N-[2-(4-Fluoro-phenoxy)-1-[1,2,4]triazol-1-ylmethyl-ethyl]-4-iodo-benzamide

In this case, the 4-fluorophenyl glycidyl ether was prepared from the tosylate epoxide in the presence of a base and this was heated with triazole to afford the secondary alcohol. Mesylate formation followed by nucleophilic displacement with azide, reduction to the corresponding amine and then standard amide coupling afforded Example 37. Mass (ESI-MS) M+1=467.0

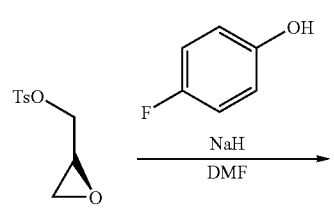

Ex 37

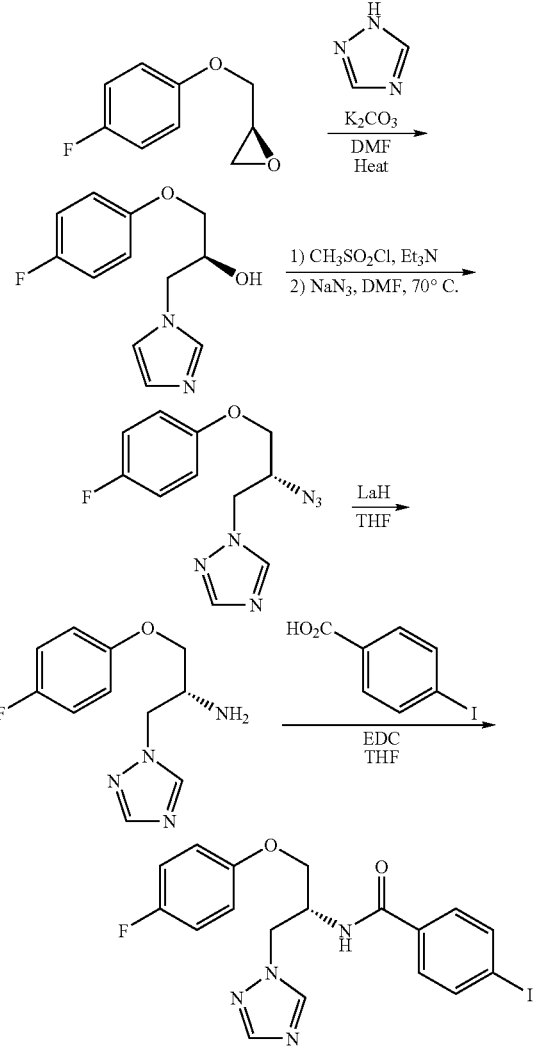

Example 38

MEK-1 Enzyme Assay

A 50 μl mixture containing 15 nM constitutively active MEK1EE and 300 nM of ERK2K52A were incubated either in the presence or absence of the compounds of the invention in 1% DMSO and 1× kinase buffer containing 3 μM ATP, 50 nM Tris-HCl pH 8.0, 10 nM MgCl$_2$, 1 mM DTT and 100 μM Na$_3$VO$_4$ in Wallac 96 well black plates for 2 hours at room temperature. At the end of the incubation the enzyme reaction was quenched by adding 50 μl of assay buffer containing 50 nM Tris-HCl, 50 mM EDTA, 0.1% BSA and a mixture of 1.25 μg/ml europium labeled anti-phosphotyrosine mAb and 5 μg/ml allophycocyanin labeled (APC) anti-GST antibody. Plates were agitated on a plate shaker for 30 minutes and phosphorylation of the ERK2K52A substrate was measured by homogenous time resolved fluorescence (HTRF) at 340 nm excitation and 665 nm (Europium)/615 nm (APC) emission filters on the VICTOR V fluorescence plate reader. The results are of phosphorylation of ERK-2, with inhibition occurring at the MEK-1 level. Results were as follows for the specified compounds:

| Tested compound | IC$_{50}$ (nM) |
|---|---|
| 4-methoxy-benzoic acid 1-imidazol-1-yl methyl-2-phenoxy-ethyl ester (racemic)<br>Example No. 6 | 1632 ± 241 |
| (R) 4-methoxy-benzoic acid 1-imidazol-1-yl methyl-2-phenoxy-ethyl ester<br>Example No. 1 | 860 ± 93 |
| (R) 4-iodo-benzoic acid 1-imidazol-1-yl methyl-2-phenoxy-ethyl ester<br>Example No. 18 | 39 ± 12 |
| 4-Iodo-benzoic acid 2-imidazol-1-yl-1-(4-nitro-phenoxymethyl)-ethyl ester (R-isomer)<br>Example No. 27 | 15 |
| (R) N-(1-imidazol-1-yl methyl-2-phenoxy-ethyl)-4-iodo-benzamide<br>Example No. 30 | 92 |
| N-[2-(4-Fluoro-phenoxy)-1-imidazol-1-ylmethyl-ethyl]-4-iodo-benzamide (R-isomer)<br>Example No. 22 | 21 |
| 4-Iodo-benzoic acid 1-imidazol-1-yl methyl-2-(pyridin-3-yloxy)-ethyl ester (R-isomer) | 11 |

Example 39

MEK-1/ERK-2 Enzyme Cascade Assay

A 50 µl mixture containing 40 nM of constitutively active MEK1EE, 160 nM of ERK2 and 10 µM MBP biotin were incubated in the presence or absence of the below compound of the invention in 1% DMSO and 1× kinase buffer containing 3 µM ATP, 50 mM Tris-HCl pH 8.0, 10 mM MgCl$_2$, 1 mM DTT, 100 µM Na$_3$VO$_4$ and 0.2 fuci $^{33}$P-γATP in Wallac 96 well white plates for 2 hours at room temperature. At the end of the incubation the enzyme reaction was quenched by adding 200 µl Phosphate buffered saline (PBS) solution containing 1.25 mg/ml Streptavidin SPA beads, 50 mM EDTA and 0.1% Triton 100 and incubated further for 12-14 hours at room temperature. $^{33}$P-γATP incorporation into MBP biotin was measured using the top counts. The assay read-out is phosphorylation of myelin basic protein, which is a representative substrate of ERK-2-phos. This assay is a further confirmatory screen of the assay of Example 38 above. Results of the assay were as follows:

| Tested compound | IC$_{50}$ (nM) |
|---|---|
| 4-methoxy-benzoic acid 1-imidazol-1-yl methyl-2-phenoxy-ethyl ester (racemic)<br>Example No. 6 | 1781 ± 254 |
| (R) 4-methoxy-benzoic acid 1-imidazol-1-yl methyl-2-phenoxy-ethyl ester<br>Example No. 1 | 920 ± 174 |
| (R) 4-iodo-benzoic acid 1-imidazol-1-yl methyl-2-phenoxy-ethyl ester<br>Example No. 27 | 36 ± 8 |
| (R) N-(1-imidazol-1-yl methyl-2-phenoxy-ethyl)-4-iodo-benzamide | 85 |

Example 40

MCF-7 and OVCAR-3 tumor cell proliferation assays

Breast cancer MCF-7 cells or ovarian cancer OVCAR-3 cells were plated in 96 well Packard white plates at 4×10$^3$ cells/well and cultured overnight at 37° C. in 5% CO$_2$. The below specified test compounds were serially diluted in 100% DMSO and subsequently added to cells to reach a final concentration of 0.5% DMSO. MCF-7 and OVCAR-3 (ATCC HTB-161) plates were incubated for an additional 4 to 5 days respectively at 37° C. and 5% CO$_2$ and cell proliferation was quantitated using the ATP lite cell proliferation kit (Packard). Results were as follows express the concentration of the compound of the invention (µM) required to inhibit the proliferation of the tumor cells by 50 percent relative untreated controls (i.e. IC$_{50}$ (µM)).

| Tested compound | IC$_{50}$ (µM) |
|---|---|
| MCF-7 assay results:<br>Example No. 6 | |
| (R) 4-methoxy-benzoic acid 1-imidazol-1-yl methyl-2-phenoxy-ethyl ester<br>Example No. 1 | 32.5 ± 3.5 |
| (R) 4-iodo-benzoic acid 1-imidazol-1-yl methyl-2-phenoxy-ethyl ester<br>OVCAR-3 assay results:<br>Example No. 6 | 15 ± 7.1 |
| (R) 4-methoxy-benzoic acid 1-imidazol-1-yl methyl-2-phenoxy-ethyl ester<br>Example No. 1 | 40 |
| (R) 4-iodo-benzoic acid 1-imidazol-1-yl methyl-2-phenoxy-ethyl ester<br>Example No. 27 | 25 |
| (R) N-(1-imidazol-1-yl methyl-2-phenoxy-ethyl)-4-iodo-benzamide | 50 |

Example 41

Colon Tumors

Compounds of the invention were tested for anti-proliferation activity against colon tumors (Colo205, HT-29, C26 and SW660 cell lines) by procedures described in Example 40 above. 2×10$^3$ cells/well used. Results were as follows again express the concentration of the test compound (µM) required to inhibit the proliferation of the tumor cells by 50 percent relative untreated controls (i.e. IC$_{50}$ (µM)).

| Tested compound | IC$_{50}$ (µM) |
|---|---|
| Colon 205 cell assay (ATCC CCL-222):<br>Example No. 6 | |
| (R) 4-methoxy-benzoic acid 1-imidazol-1-yl methyl-2-phenoxy-ethyl ester<br>Example No. 1 | 22.5 |
| (R) 4-iodo-benzoic acid 1-imidazol-1-yl methyl-2-phenoxy-ethyl ester | 1.4 |

-continued

| Tested compound | IC$_{50}$ (µM) |
|---|---|
| Example No. 27 | |
| (R) N-(1-imidazol-1-yl methyl-2-phenoxy-ethyl)-4-iodo-benzamide | 2.1 |
| HT-29 cell assay (ATCC HTB-38): | |
| Example No. 6 | |
| (R) 4-methoxy-benzoic acid 1-imidazol-1-yl methyl-2-phenoxy-ethyl ester | 27.5 |
| Example No. 1 | |
| (R) 4-iodo-benzoic acid 1-imidazol-1-yl methyl-2-phenoxy-ethyl ester | 3.5 |
| Example No. 27 | |
| (R) N-(1-imidazol-1-yl methyl-2-phenoxy-ethyl)-4-iodo-benzamide | 2.8 |
| SW 660 cell assay (ATCC CCL-227): | |
| Example No. 6 | |
| (R) 4-methoxy-benzoic acid 1-imidazol-1-yl methyl-2-phenoxy-ethyl ester | 20 |
| Example No. 1 | |
| (R) 4-iodo-benzoic acid 1-imidazol-1-yl methyl-2-phenoxy-ethyl ester | 2.1 |
| Example No. 27 | |
| (R) N-(1-imidazol-1-yl methyl-2-phenoxy-ethyl)-4-iodo-benzamide | 2.2 |
| Colon C26 cell assay: | |
| Example No. 1 | |
| 4-Iodo-benzoic acid 1-imidazol-1-yl methyl-2-phenoxy-ethyl ester | 2.33 |
| Example No. 18 | |
| 4-Iodo-benzoic acid 2-imidazol-1-yl-1-(4-nitro-phenoxymethyl)-ethyl ester (R-isomer | 0.57 |
| Example No. 22 | |
| 4-Iodo-benzoic acid 1-imidazol-1-yl methyl-2-(pyridin-3-yloxy)-ethyl ester (R-isomer) | 1.08 |
| Example No. 34 | |
| N-[1-(2-Chloro-imidazol-1-ylmethyl)-2-(4-fluoro-phenoxy)-ethy]-4-iodo-benzamide (R-isomer) | 1.25 |
| Example No. 35 | |
| N-[1-(2-Chloro-imidazol-1-ylmethyl)-2-(4-cyano-phenoxy)-ethyl]-4-iodo-benzamide | 0.30 |

Example 42

Additional Tumors (R) 4-iodo-benzoic acid 1-imidazol-1-yl methyl-2-phenoxy-ethyl ester (Example No. 1) was tested for anti-proliferation activity against additional tumor cell types as specified below by procedures described in Example 39 above. American Type Culture Collection (ATCC) deposit numbers are indicated below for many of the tested cell types. Results express, as follows, the concentration of compound of the invention (µM) required to inhibit the proliferation of the tumor cells by 50 percent relative untreated controls (i.e. IC$_{50}$ (µM)).

| Tumor | IC$_{50}$ (µM) |
|---|---|
| Breast Adeno Carcinoma (MCF-7 cell line) | 33 |
| Breast Ductal Carcinoma (T47D cell line; ATCC HTB-133) | 11 |
| Colon Adeno Carcinoma (DLD-1 cell line; ATCC CCL-221) | 36 |
| Colon Adeno Carcinoma (Grade II) (HT-29 cell line; ATCC HTB-38) | 4 |
| Kidney Carcinoma (A498 cell line; ATCC HTB-44) | 54 |
| Kidney Adeno Carcinoma (ACHN cell line; ATCC CRL-1611) | >100 |
| Promyelocytic Leukemia (HL-60 cell line; ATCC CRL-240) | 3.6 |
| Chronic Myelogenous Leukemia (K562 cell line; ATCC CCL-243) | 33 |
| Lung Carcinoma (A549 cell line; ATCC CCL-185) | 25 |
| Lung Carcinoma (PC-6 cell line) | 43 |
| Malignant Melanoma (SK-MEL-5 cell line; ATCC HTB-70) | 11 |
| Neuroepithelioma (SK-N-MC cell line; ATCC HTB-10) | 6.7 |
| Pancreatic Carcinoma (MIA PaCa-2 cell line; ATCC CRL-1420) | 3.1 |
| Pancreatic Epithelioid Carcinoma (PANC-1 cell line; ATCC CRL-1469) | >100 |
| Prostate Adenocarcinoma (PC-3 cell line; ATCC CRL-1435) | 24 |

Example 43

Rat Granulosa Cell Assay (R) 4-iodo-benzoic acid 1-imidazol-1-yl methyl-2-phenoxy-ethyl ester (Example No. 1) was tested in a primary rat granulosa cell bioassay for activation of follicle-stimulating hormone (FSH). This in vitro assay detects conversion of androstendione to estrogen by granulosa cells in the presence of FSH was measured using a radio immunoassay (RIA) to detect the production of estradiol, which occurs in the presence of at least nanomolar concentrations of FSH (Johanson et al. *Acta Endocrinologica*, 1988, 117(4), 497-506).

Cells were plated at 5000, 8,000 and 20,000 cells/well/200 µl of GAB medium on poly-D-lysine coated 96-well tissue culture plates. Plates were incubated at 37° C. in a 5% CO/95% air incubator for 3 days. Cultures were washed prior to stimulation with the test compound ((R) 4-iodo-benzoic acid 1-imidazol-1-yl methyl-2-phenoxy-ethyl ester) Example 1 in the presence of FSH in concentrations of 2 picomolar to 5 picomolar. The compound of the invention and picomolar FSH were then added to the cultures. Cells were incubated @ 37° C. in 5% CO$_2$. Three days later, cell supernatants were collected and diluted 1:100 in GAB medium for measurement of estradiol by RIA. The RIA was performed according to manufacturer directions except that an estradiol standard was prepared in absolute ethanol at 100 ng/ml and then further diluted in GAB medium, instead of kit buffer.

Results show that (R) 4-iodo-benzoic acid 1-imidazol-1-yl methyl-2-phenoxy-ethyl ester (Example 1) at concentrations of 10 nM to 100 nM induces estradiol production in the presence of the picomolar FSH.

Example 44

Inhibition of TNF-alpha production in LPS-stimulated mice

Endotoxins are the lipopolysaccharides (LPS) constituents of the outer membrane of Gram negative bacteria. Response to LPS has been shown to involve the activation of different cell populations and to lead to the expression of various inflammatory cytokines that include tumor necrosis factor-alpha (TNFα) and interferon gamma (IFN-γ).

As LPS is known to stimulate the activation of various MAP kinase pathways, including ERK1/2 (Rao et al. *Journal of Toxicology and Environmental Health*, Part A, 2002, 65(10), 757-768) the ability of ERK/MEK inhibitors can be tested after the ERK signaling pathway has been switched on by a LPS challenge.

Injection of lipopolysaccharide (LPS) induces a rapid release of soluble tumor necrosis factor (TNF-α) into the periphery. This model is used to identify potential blockers of TNF release in vivo The potency of compounds of the invention as inhibitors of serum TNFα elevation in mice treated with LPS is determined as follows:

For per oral (p.o.) administration, compounds of the invention are formulated in 0.5% carboxymethyl cellulose/0.25% Tween 80 in saline and given orally via gavage 15 in prior to LPS administration. Dexamethasone is used as the reference compound and given at 0.1 mg/kg per orally.

C3/hen female mice (Iffa-Credo, France) are injected intraperitoneally with 0.3 mg/kg LPS (*Escherichia coli*, Serotype 0111:B4, Sigma Chemical Co., St. Louis, Mo.) and sacrificed 90 min later by CO2 asphyxiation. Blood is immediately taken from caudal vena cava and plasma prepared and frozen at −80° C. Each group of treatment contained 6 animals.

Table I below shows the percentage of inhibition of TNF release in LPS-induced mice versus control animals.

TABLE 1

| Compound | Dose (mg/kg) | Timing | TNF Release vs LPS inj. % of inhibition Mean ± SEM |
|---|---|---|---|
| Example 27 | 50 | −15 mn | 39 ± 3 |
|  | 12.5 | −15 mn | 32 ± 5 |
| Example 30 | 50 | −15 mn | 85 ± 3 |
|  | 12.5 | −15 mn | 77 ± 2 |
| Dexamethasone | 0.1 | −15 mn | 86 ± 6 |
|  | 0.1 | −15 mn | 88 ± 1 |

Agents of the invention inhibit TNF production to the extent from about 39% up to about 85% in the above study when administered at 50 mg/mg p.o.

Example 45

Effects of MEK Inhibitors on the Growth of Tumors Induced in CDF1 Mice with Murine Colon Carcinoma C26 Cells The aim of this study was to evaluate the effects of Example No. 30 in FIG. 1: N-(-1-imidazol-1-ylmethyl-2-phenoxy-ethyl)-4-iodo-benzamide (R-isomer) given at 50 mg/kg (triangles) and 100 mg/kg (squares) p.o. bid. Control group (empty circles) was treated with NP3S (5% N-methylpyrrolidone/30% PEG400/25% PEG200/20% Propylene Glycol in Saline) per os bid. Cyclophosphamide (50 mg/kg s.c administered every third day for a total of 5 treatments) was used as reference compound.

Drugs treatment started 8 days following C26 cell injection and then continued for 13 days. The experiment was stopped at this point, i.e. after 13 days of treatment (corresponding to 20 days after tumor cell inoculation) when tumor size was more than the 10% of mouse body weight.

Tumor volume and body weight were monitored every three days from day 8 until day 20. To achieve information on plasma levels, at the end of experiment (1 hour after the first administration and 1 h after the second one of the last day dosing), blood samples were collected from animals receiving Example No. 30.

When compared to the NP3S control group, Example No. 30 significantly (starting from day 11 [**]−p>0.01, 14 [*] and 20 [***]−p<0.05, 17−p<0.001) * reduced tumor growth at the dose of 100 mg/kg. The inhibition of tumor growth rate evaluated at day 20 was 37%. (FIG. 1A). In addition, significant prevention of tumor-induced body weight loss was obtained after treatment at 50 and 100 mg/kg (FIG. 1B)

*One-way Anova followed by Tukey test

Cyclophosphamide significantly slowed down tumor growth. Significant differences in tumor volume were observed starting from day 11 until day 20 (p<0.001). The inhibition of tumor growth at day 20 was 73%. Like the tumor growth, also tumor-associated loss in body weight was markedly prevented from day 11.

The protective effects on tumor-induced body weight loss, observed sometimes in absence of an evident inhibitory effect on tumor mass, could be related to the effects of MEK inhibitors in blocking the release of cytokines, such as TNFα, IL-6 or LIF, involved in cancer cachexia, and likely involved in the lipolytic activity (Hidekuni I. et al, Int. J. Cancer, 2002).

What is claimed is:

1. A method for treating a mammal suffering from or susceptible to a cancer selected from the group consisting of breast cancer, ovarian cancer, and colon cancer, comprising administering to the mammal in need of said treating an effective of amount of a compound of the following Formula I:

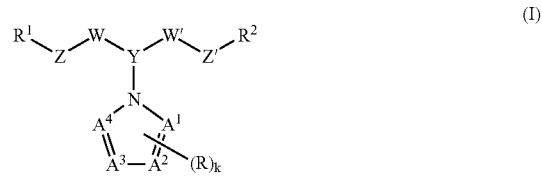

(I)

wherein each of $A^1$, $A^2$, and $A^4$ are carbon and $A^3$ is nitrogen;

each R is independently halo, nitro, optionally substituted alkyl; optionally substituted alkenyl; optionally substituted alkynyl; optionally substituted heteroalkyl; optionally substituted heteroalkenyl; optionally substituted heteroalkynyl; optionally substituted alkanol; optionally substituted aryl, optionally substituted heteroalicyclic, optionally substituted heteroaromatic, optionally substituted aralkyl; optionally substituted heteroarylalkyl; and optionally substituted heteroalicyclicalkyl;

or two R groups on adjacent ring atoms are taken together with the ring atoms to which they are bonded to form a fused alicyclic, heteroalicylic, aryl or heteraromatic group having from 4 to about 8 ring members;

k is an integer;

Y is selected from the group consisting of $CH_2CH$, $CH_2CH(CH_2)_q$, $CH_2CR^7CH_2$, and a branched alkyl having the formula $CH_2CH(CH_2)_p(CH_2)_s$, wherein $R^7$ is H or $C_1$-$C_6$ alkyl, s and p are the same or different and are zero or a positive integer, and q is a positive integer;

W and W' are each independently a heteroatom; optionally substituted heteroalkyl; optionally substituted heteroalkenyl; and optionally substituted heteroalkynyl;

Z and Z' are each independently a chemical bond or alkanoyl; $R^1$ and $R^2$ are each independently optionally substituted aryl or optionally substituted heteroaromatic; and a pharmaceutically acceptable salt or enantiomer thereof, with the caveat that the compound of Formula I is not a racemate of 4-methoxy benzoic acid 1-imidazol-1-yl methyl-2-phenoxy ethyl ester, 4-chloro benzoic acid 1-imidazol-1-yl methyl-2-phenoxy-ethyl ester, or benzoic acid 1-imidazol-1-yl methyl-2-phenoxy-ethyl ester.

2. The method of claim 1, wherein when $R^2$ is aryl and said aryl is phenyl, said phenyl optionally is substituted.

3. The method of claim 1, wherein the compound of Formula (I) is a compound of the following Formula (II):

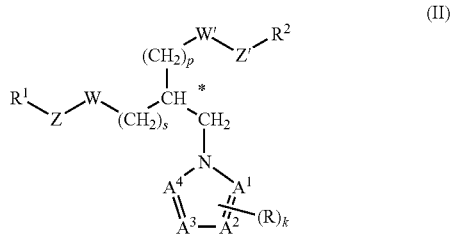

wherein each of $A^1$, $A^2$, and $A^4$ are carbon and $A^3$ is nitrogen;

each R is independently halo, nitro, optionally substituted alkyl; optionally substituted alkenyl; optionally substituted alkynyl; optionally substituted heteroalkyl; optionally substituted heteroalkenyl; optionally substituted heteroalkynyl; optionally substituted alkanol; optionally substituted aryl, optionally substituted heteroalicyclic, optionally substituted heteroaromatic, optionally substituted aralkyl; optionally substituted heteroarylalkyl; and optionally substituted heteroalicyclicalkyl;

or two R groups on adjacent ring atoms are taken together with the ring atoms to which they are bonded to form a fused alicyclic, heteroalicyclic, aryl or heteraromatic group having from 4 to about 8 ring members;

k is an integer;

s and p are the same or different and are zero or a positive integer;

W and W' are each independently a hetero atom; optionally substituted heteroalkyl; optionally substituted heteroalkenyl; and optionally substituted heteroalkynyl;

Z and Z' are each independently a chemical bond or alkanoyl;

$R^1$ and $R^2$ are each independently optionally substituted aryl or optionally substituted heteroaromatic, wherein when $R^2$ is aryl and said aryl is phenyl, said phenyl optionally is substituted; or a pharmaceutically acceptable salt or enantiomer thereof.

4. The method of claim 3, wherein q is 1.

5. The method of claim 3, wherein said compound is N-[1-(4-Cyano-phenoxymethyl)-2-imidazol-1-yl-ethyl]-4-iodo-benzamide.

6. The method of claim 1, wherein the compound of Formula (I) is a compound of the following Formula (III):

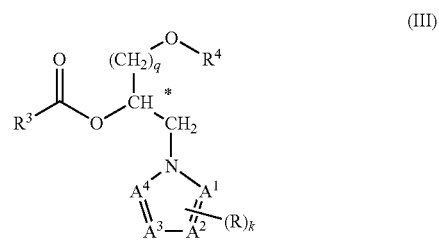

wherein each of $A^1$, $A^2$, and $A^4$ is carbon and $A^3$ is nitrogen;

each R is independently halo, nitro, optionally substituted alkyl; optionally substituted alkenyl; optionally substituted alkynyl; optionally substituted heteroalkyl; optionally substituted heteroalkenyl; optionally substituted heteroalkynyl; optionally substituted alkanol; optionally substituted aryl, optionally substituted heteroalicyclic, optionally substituted heteroaromatic, optionally substituted aralkyl; optionally substituted heteroarylalkyl; and optionally substituted heteroalicyclicalkyl;

or two R groups on adjacent ring atoms are taken together with the ring atoms to which they are bonded to form a fused alicyclic, heteroalicyclic, aryl or heteraromatic group having from 4 to about 8 ring members;

k is an integer;

q is a positive integer, $R^3$ and $R^4$ are each optionally substituted aryl or optionally substituted heteroaromatic, wherein when $R^4$ is aryl and said aryl is phenyl, said phenyl optionally is substituted; or a pharmaceutically acceptable salt or enantiomer thereof.

7. The method of claim 6, wherein q is 1.

8. The method of claim 1, wherein the compound of Formula (I) is a compound of the following Formula (IV):

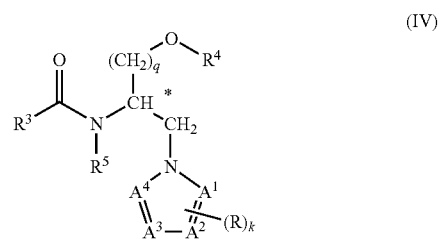

wherein each of $A^1$, $A^2$, and $A^4$ is carbon and $A^3$ is nitrogen;

each R is independently halo, nitro, optionally substituted alkyl; optionally substituted alkenyl; optionally substituted alkynyl; optionally substituted heteroalkyl; optionally substituted heteroalkenyl; optionally substituted heteroalkynyl; optionally substituted alkanol; optionally substituted aryl, optionally substituted heteroalicyclic, optionally substituted heteroaromatic, optionally substituted aralkyl; optionally substituted heteroarylalkyl; and optionally substituted heteroalicyclicalkyl;

or two R groups on adjacent ring atoms are taken together with the ring atoms to which they are bonded to form a fused alicyclic, heteroalicyclic, aryl or heteraromatic group having from 4 to about 8 ring members;

k is an integer;

q is a positive integer;

$R^3$ and $R^4$ are each optionally substituted aryl or optionally substituted heteroaromatic, wherein when $R^4$ is aryl and said aryl is phenyl, said phenyl optionally is substituted;

$R^5$ is hydrogen, optionally substituted alkyl; optionally substituted alkenyl; optionally substituted alkynyl; optionally substituted heteroalkyl; optionally substituted heteroalkenyl; or optionally substituted heteroalkynyl; optionally substituted aryl or optionally substituted heteroaromatic; or a pharmaceutically acceptable salt or enantiomer thereof.

9. The method of claim 1, wherein the compound of Formula (I) is a compound of the following Formula (V):

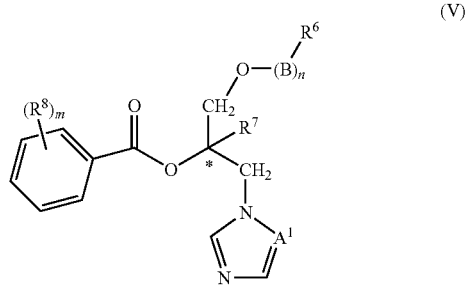

wherein $A^1$ is $CR^9$ where $R^9$ is H, $C_1$-$C_6$ alkyl, aryl or halogen;

B is —C(O)—;

$R^6$ is $C_1$-$C_6$ alkyl, $C_3$-$C_6$ cycloalkyl $C_1$-$C_6$ alkyl, $C_3$-$C_6$ heterocycloalkyl, aryl or heteroaryl;

$R^7$ is H or $C_1$-$C_6$ alkyl;

$R^8$ is $C_1$-$C_6$ alkyl, $C_1$-$C_6$ alkoxy or halogen;

n is 0 or 1;

m is 1 or 2; or a pharmaceutically acceptable salt or enantiomer thereof.

10. The method of claim 9, wherein $A^1$ is $CR^9$; $R^9$ is H, $C_1$-$C_6$ alkyl or halogen; $R^6$ is aryl or heteroaryl; $R^7$ is H or $C_1$-$C_6$ alkyl; $R^8$ is substituted $C_1$-$C_6$ alkyl, $C_1$-$C_6$ alkoxy or halogen; n is 0; m is 1 or 2.

11. The method of claim 10, wherein $A^1$ is $CR^9$; $R^9$ is H, $C_1$-$C_6$ alkyl or halogen; $R^6$ is aryl or heteroaryl; $R^7$ is H; $R_8$ is $C_1$-$C_6$ alkyl, $C_1$-$C_6$ alkoxy or halogen; n is 0; m is 1 or 2.

12. The method of claim 1, wherein the compound of Formula (I) is a compound of the following Formula (VI):

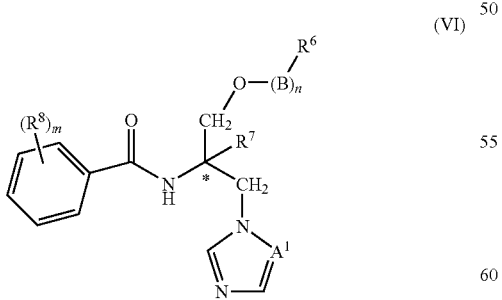

wherein $A^1$ is $CR^9$ $R^9$ is H, $C_1$-$C_6$ alkyl, $C_1$-$C_6$ alkyl, aryl or halogen; B is —C(O)—;

$R^6$ is $C_1$-$C_6$ alkyl, $C_3$-$C_6$ cycloalkyl-$C_1$-$C_6$ alkyl, $C_3$-$C_6$ heterocycloalkyl, aryl or heteroaryl;

$R^7$ is H or $C_1$-$C_6$ alkyl;

$R^8$ is $C_1$-$C_6$ alkyl, $C_1$-$C_6$ alkoxy or halogen;

n is 0 or 1;

m is 1 or 2; or a pharmaceutically acceptable salt or enantiomer thereof.

13. The method of claim 12, wherein $A^1$ is $CR^9$; $R^9$ is H, $C_1$-$C_6$ alkyl or halogen; $R^6$ is aryl or heteroaryl; $R^7$ is H or $C_1$-$C_6$ alkyl; $R^8$ is substituted $C_1$-$C_6$ alkyl, $C_1$-$C_6$ alkoxy or halogen; n is 0; m is 1 or 2.

14. The method of claim 1, wherein the compound, or a pharmaceutically acceptable salt or enantiomer thereof, is selected from the group consisting of:

4-methoxy-benzoic acid 1-imidazol-1-yl methyl-2-(4-fluorophenoxy)-ethyl ester;

3-methoxy-benzoic acid 1-imidazol-1-yl methyl-2-phenoxy-ethyl ester;

4-methoxy-benzoic acid 1-imidazol-1-yl methyl-2-(4-methoxy phenoxy)-ethyl ester;

4-methoxy-benzoic acid 1-imidazol-1-yl methyl-2-(4-iodophenoxy)-ethyl ester;

4-iodo-benzoic acid 1-imidazol-1-yl methyl-2-(4-iodo phenoxy)-ethyl ester;

4-bromo-2-chloro-benzoic acid 1-imidazol-1-yl methyl-2-phenoxy)-ethyl ester;

4-bromo-2-chloro-benzoic acid 1-imidazol-1-yl methyl-2-(4-iodophenoxy)-ethyl ester;

4-bromo-benzoic acid 1-imidazol-1-yl methyl-2-phenoxy-ethyl ester;

4-trifluoromethyl-benzoic acid 1-imidazol-1-yl methyl-2-phenoxy-ethyl ester;

N-(1-imidazol-1-yl methyl-2-phenoxy-ethyl)-4-methoxy-benzamide;

4-iodo-benzoic acid 1-imidazol-1-yl methyl-2-(4-fluorophenoxy)-ethyl ester;

4-fluoro-benzoic acid 1-imidazol-1-yl methyl-2-phenoxy-ethyl ester;

N-[(1-imidazol-1-yl methyl)-2-phenoxy-ethyl]-N-methyl-4-iodo-benzamide;

N-[(1-imidazol-1-yl methyl)-2-(4-fluorophenoxy-ethyl)]-N-methyl-4-iodobenzamide;

4-Iodo-benzoic acid 2-(4-acetylamino-phenoxy)-1-imidazol-1-ylmethyl-ethyl ester (R-isomer);

N-[2-(4-Fluoro-phenoxy)-1-imidazol-1-ylmethyl-ethyl]-4-iodo-benzamide (R-isomer);

N-[2-(4-tert-Butyl-phenoxy)-1-imidazol-1-ylmethyl-ethyl]-4-iodo-benzamide;

4-Iodo-benzoic acid 2-imidazol-1-yl-1-(3-nitro-phenoxymethyl)-ethyl ester (R-isomer);

4-Iodo-benzoic acid 2-imidazol-1-yl-1-(2-nitro-phenoxymethyl)-ethyl ester (R-isomer);

4-Iodo-benzoic acid 1-(4-nitrobenzoyloxymethyl)-2-imidazol-1-yl-1-methyl-ethyl ester (R-isomer);

4-Iodo-benzoic acid 2-imidazol-1yl-1-(4-nitro-phenoxymethyl)-ethyl ester (R-isomer);

4-Iodo-benzoic acid 1-imidazol-1-ylmethyl-2-methoxy-ethyl ester (R-isomer);

4-Iodo-benzoic acid 1-(2-methyl-imidazol-1-ylmethyl)-2-(tetrahydro-pyran-2-yloxy)-ethyl ester;

4-Iodo-benzoic acid 1-imidazol-1-yl methyl-2-(pyridin-3-yloxy)-ethyl ester (R-isomer);

2,4-Dichloro-benzoic acid 2-(4-fluoro-phenoxy)-1-imidazol-1-ylmethyl-ethyl ester (R-isomer);

4-Iodo-benzoic acid 1-(4-cyano-phenoxymethyl)-2-imidazol-1-yl-ethyl ester;

4-Iodo-benzoic acid 1-(4-cyano-phenoxymethyl)-2-(2-methyl-imidazol-1-yl)-ethyl ester (R-isomer);

2-Chloro-N-[2-(4-fluoro-phenoxy)-1-imidazol-1-ylmethyl-ethyl]-4-iodo-benzamide (R-isomer);

N-[2-(4-Fluoro-phenoxy)-1-(2-methyl-imidazol-1-ylmethyl)-ethyl]-4-iodo-benzamide (R-isomer);

2-Chloro-4-iodo-benzoic acid 1-cyclopropylmethoxymethyl-2-(2-methyl-imidazol-1-yl)-ethyl ester (R-isomer);
N-[1-(2-Chloro-imidazol-1-ylmethyl)-2-(4-fluoro-phenoxy)-ethyl]-4-iodo-benzamide (R-isomer);
N-[2-(4-Fluoro-phenoxy)-1-imidazol-1-ylmethyl-ethyl]-3-iodo-benzamide;
2-Chloro-N-[2-imidazol-1-yl-1-(pyridin-3-yloxymethyl)-ethyl]-4-iodo-benzamide;
N-[2-Imidazol-1-yl-1-(pyridin-3-yloxymethyl)-ethyl]-4-iodo-benzamide;
N-[2-(4-Fluoro-phenoxy)-1-(2-phenyl-imidazol-1-ylmethyl)-ethyl]-4-iodo-benzamide;
N-[1-(2-Chloro-imidazol-1-ylmethyl)-2-(4-cyano-phenoxy)-ethyl]-4-iodo-benzamide;
N-[2-Imidazol-1-yl-1-(3-nitro-pyridin-2-yloxymethyl)-ethyl]-4-iodo-benzamide;
N-[2-Imidazol-1-yl-1-(4-nitro-phenoxymethyl)-ethyl]-4-iodo-benzamide;
N-[1-(3-Cyano-pyridin-2-yloxymethyl)-2-imidazol-1-yl-ethyl]-4-iodo-benzamide;
N-[1-(5-Cyano-pyridin-2-yloxymethyl)-2-imidazol-1-yl-ethyl]-4-iodo-benzamide;
N-[1-(4-Cyano-phenoxymethyl)-2-imidazol-1-yl-ethyl]-4-iodo-benzamide;
N-[1-(4-Cyano-phenoxymethyl)-2-(2-methyl-imidazol-1-yl)-ethyl]-4-iodo-benzamide; and
N-[1-(2-Difluoromethyl-imidazol-1-ylmethyl)-2-(4-fluoro-phenoxy)-ethyl]-4-iodo-benzamide.

15. The method of claim 1, wherein the compound is 4-iodo-benzoic acid 1-imidazol-1-yl methyl-2-phenoxy-ethyl ester, or a pharmaceutically acceptable salt or enantiomer thereof.

16. The method of claim 1, wherein the compound is N-[(1-imidazol-1-yl methyl)-2-phenoxy-ethyl]-4-iodo-benzamide, or a pharmaceutically acceptable salt or enantiomer thereof.

17. The method of claim 1, wherein the compound is present in an enantiomeric excess.

18. The method of claim 1, wherein the compound of Formula (I) is a compound of the following Formula (VII):

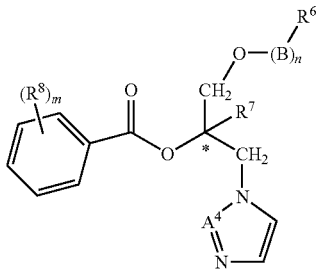

(VII)

wherein $A^4$ is $CR^9$;
$R^9$ is H, $C_1$-$C_6$ alkyl, $C_1$-$C_6$ alkyl, aryl or halogen;
B is —C(O)—;
$R^6$ is $C_1$-$C_6$ alkyl, $C_3$-$C_6$ cycloalkyl $C_1$-$C_6$ alkyl, $C_3$-$C_6$ heterocycloalkyl, aryl or heteroaryl;
$R^7$ is H or $C_1$-$C_6$ alkyl;
$R^8$ is $C_1$-$C_6$ alkyl, $C_1$-$C_6$ alkoxy or halogen;
n is 0 or 1;
m is 1 or 2; or a pharmaceutically acceptable salt or enantiomer thereof.

19. The method of claim 18, wherein $A^4$ is $CR^9$; $R^9$ is H, $C_1$-$C_6$ alkyl or halogen; $R^6$ is aryl or heteroaryl; $R^7$ is H or $C_1$-$C_6$ alkyl; $R^8$ is $C_1$-$C_6$ alkyl, $C_1$-$C_6$ alkoxy or halogen; n is 0 or 1; m is 1 or 2.

20. The method of claim 19, wherein $A^4$ is $CR^9$; $R^9$ is H, $C_1$-$C_6$ alkyl or halogen; $R^6$ is aryl or heteroaryl; $R^7$ is H; $R_8$ is $C_1$-$C_6$ alkyl, $C_1$-$C_6$ alkoxy or halogen; n is 0; m is 1 or 2.

21. The method of claim 1, wherein the compound of Formula (I) is a compound of the following Formula (VIII):

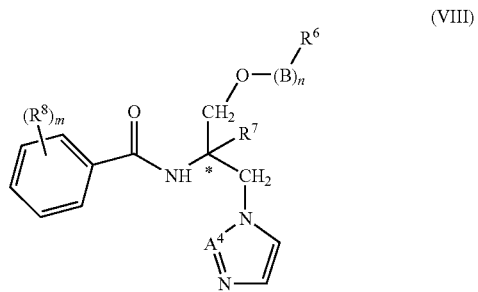

(VIII)

wherein $A^4$ is $CR^9$;
$R^9$ is H, $C_1$-$C_6$ alkyl, $C_1$-$C_6$ alkyl, aryl or halogen;
B is —C(O)—;
$R^6$ is $C_1$-$C_6$ alkyl, $C_3$-$C_6$ cycloalkyl $C_1$-$C_6$ alkyl, $C_3$-$C_6$ heterocycloalkyl, aryl or heteroaryl;
$R_7$ is H or $C_1$-$C_6$ alkyl;
$R^8$ is $C_1$-$C_6$ alkyl, $C_1$-$C_6$ alkoxy or halogen;
n is 0 or 1;
m is 1 or 2; or a pharmaceutically acceptable salt or enantiomer thereof.

22. The method of claim 21, wherein $A^4$ is $CR^9$; $R^9$ is H, $C_1$-$C_6$ alkyl or halogen; $R^6$ is aryl or heteroaryl; $R^7$ is H or $C_1$-$C_6$ alkyl; $R^8$ is $C_1$-$C_6$ alkyl, $C_1$-$C_6$ alkoxy or halogen; n is 0 or 1; m is 1 or 2.

23. The method of claim 1, wherein said mammal is a human.

24. The method of claim 1, wherein said form of cancer is breast cancer.

25. The method of claim 1, wherein said form of cancer is ovarian cancer.

26. The method of claim 1, wherein said form of cancer is colon cancer.

* * * * *